(12) United States Patent
Flanner et al.

(10) Patent No.: US 8,357,394 B2
(45) Date of Patent: Jan. 22, 2013

(54) COMPOSITIONS AND METHODS FOR IMPROVED EFFICACY OF PENICILLIN-TYPE ANTIBIOTICS

(75) Inventors: Henry H. Flanner, Montgomery Village, MD (US); Robert J. Guttendorf, Gaitherburg, MD (US); Susan P. Clausen, Ijamsville, MD (US); Donald Treacy, Woodbine, MD (US); Beth A. Burnside, Bethesda, MD (US)

(73) Assignee: Shionogi Inc., Florham Park, NJ (US)

( * ) Notice: Subject to any disclaimer, the term of this patent is extended or adjusted under 35 U.S.C. 154(b) by 0 days.

(21) Appl. No.: 11/636,291

(22) Filed: Dec. 8, 2006

(65) Prior Publication Data

US 2007/0134327 A1    Jun. 14, 2007

Related U.S. Application Data

(60) Provisional application No. 60/748,660, filed on Dec. 8, 2005.

(51) Int. Cl.
    *A61K 9/20* (2006.01)
(52) U.S. Cl. ........................................ 424/464
(58) Field of Classification Search .................. None
    See application file for complete search history.

(56) References Cited

U.S. PATENT DOCUMENTS

| | | |
|---|---|---|
| 1,330,829 A | 2/1920 | Wilson |
| 3,108,046 A | 10/1963 | Harbit |
| 3,870,790 A | 3/1975 | Lowey et al. |
| 4,007,174 A | 2/1977 | Laundon |
| 4,008,246 A | 2/1977 | Ochiai et al. |
| 4,018,918 A | 4/1977 | Ayer et al. |
| 4,048,306 A | 9/1977 | Maier et al. |
| 4,131,672 A | 12/1978 | Huffman |
| 4,175,125 A | 11/1979 | Huffman |
| 4,226,849 A | 10/1980 | Schor |
| 4,236,211 A | 11/1980 | Arvesen |
| 4,250,166 A | 2/1981 | Maekawa et al. |
| 4,331,803 A | 5/1982 | Watanabe et al. |
| 4,362,731 A | 12/1982 | Hill |
| 4,369,172 A | 1/1983 | Schor et al. |
| 4,399,151 A | 8/1983 | Sjoerdsma et al. |

(Continued)

FOREIGN PATENT DOCUMENTS

EP    0052075    11/1981

(Continued)

OTHER PUBLICATIONS

Kaye et al, The Clinical Pharmacokinetics of a New Pharmacokinetically Enhanced Formulation of Amoxicillin/Clavulanate, Clinical Therapeutics, 2001, 23(4), 578-584.*

(Continued)

*Primary Examiner* — Paul Dickinson
(74) *Attorney, Agent, or Firm* — MH2 Technology Law Group LLP

(57) ABSTRACT

Disclosed are once-a-day penicillin-type antibiotic products comprising at least one modified release dosage form comprising penicillin-type antibiotics and pharmaceutically acceptable carriers, which compositions provide T>$MIC_{90}$ in the serum for at least 5 hours (preferably for at least five consecutive hours), within a 24-hour dosing interval, for a given bacterial pathogen's $MIC_{90}$, while providing a total dosage of the penicillin-type antibiotic for a 24-hour dosing interval.

7 Claims, 1 Drawing Sheet

U.S. PATENT DOCUMENTS

| | | |
|---|---|---|
| 4,430,495 A | 2/1984 | Patt et al. |
| 4,435,173 A | 3/1984 | Siposs et al. |
| 4,474,768 A | 10/1984 | Bright |
| 4,517,359 A | 5/1985 | Kobrehel et al. |
| 4,525,352 A | 6/1985 | Cole et al. |
| 4,529,720 A | 7/1985 | Cole et al. |
| 4,560,552 A | 12/1985 | Cole et al. |
| 4,568,741 A | 2/1986 | Livingston |
| 4,598,045 A | 7/1986 | Masover et al. |
| 4,616,008 A | 10/1986 | Hirai et al. |
| 4,634,697 A | 1/1987 | Hamashima |
| 4,644,031 A | 2/1987 | Lehmann et al. |
| 4,670,549 A | 6/1987 | Morimoto et al. |
| 4,672,109 A | 6/1987 | Watanabe et al. |
| 4,680,386 A | 7/1987 | Morimoto et al. |
| 4,710,565 A | 12/1987 | Livingston et al. |
| 4,723,958 A | 2/1988 | Pope et al. |
| 4,728,512 A | 3/1988 | Mehta et al. |
| 4,749,568 A | 6/1988 | Reusser et al. |
| 4,755,385 A | 7/1988 | Etienne et al. |
| 4,775,751 A | 10/1988 | McShane |
| 4,794,001 A | 12/1988 | Mehta et al. |
| 4,808,411 A | 2/1989 | Lu et al. |
| 4,812,561 A | 3/1989 | Hamashima et al. |
| 4,828,836 A | 5/1989 | Elger et al. |
| 4,831,025 A | 5/1989 | Godtfredsen et al. |
| 4,835,140 A | 5/1989 | Smith et al. |
| 4,842,866 A | 6/1989 | Horder et al. |
| 4,849,515 A | 7/1989 | Matier et al. |
| 4,879,135 A | 11/1989 | Greco et al. |
| 4,894,119 A | 1/1990 | Baron, Jr. et al. |
| 4,895,934 A | 1/1990 | Matier et al. |
| 4,904,476 A | 2/1990 | Mehta et al. |
| 4,915,953 A | 4/1990 | Jordan et al. |
| 4,945,080 A | 7/1990 | Lindstrom et al. |
| 4,945,405 A | 7/1990 | Hirota |
| 4,971,805 A | 11/1990 | Kitanishi et al. |
| 4,990,602 A | 2/1991 | Morimoto et al. |
| 5,011,692 A | 4/1991 | Fujiota et al. |
| 5,045,533 A | 9/1991 | Philippe et al. |
| 5,051,262 A | 9/1991 | Panoz et al. |
| 5,110,597 A | 5/1992 | Wong et al. |
| 5,110,598 A | 5/1992 | Kwan et al. |
| 5,143,661 A | 9/1992 | Lawter et al. |
| 5,158,777 A | 10/1992 | Abramowitz et al. |
| 5,178,874 A | 1/1993 | Kwan et al. |
| 5,182,374 A | 1/1993 | Tobkes et al. |
| 5,200,193 A | 4/1993 | Radebaugh et al. |
| 5,204,055 A | 4/1993 | Sachs et al. |
| 5,213,808 A | 5/1993 | Bar-Shalom et al. |
| 5,229,131 A | 7/1993 | Amidon et al. |
| 5,230,703 A | 7/1993 | Alon |
| 5,274,085 A | 12/1993 | Amano et al. |
| 5,288,503 A | 2/1994 | Wood et al. |
| 5,334,590 A | 8/1994 | DiNinno et al. |
| 5,340,656 A | 8/1994 | Sachs et al. |
| 5,358,713 A | 10/1994 | Shimamura |
| 5,387,380 A | 2/1995 | Cima et al. |
| 5,393,765 A | 2/1995 | Infeld et al. |
| 5,395,626 A | 3/1995 | Kotwal et al. |
| 5,395,628 A | 3/1995 | Noda et al. |
| 5,399,723 A | 3/1995 | Iinuma et al. |
| 5,401,512 A | 3/1995 | Rhodes et al. |
| 5,407,686 A | 4/1995 | Patel et al. |
| 5,413,777 A | 5/1995 | Sheth et al. |
| 5,414,014 A | 5/1995 | Schneider et al. |
| 5,422,343 A | 6/1995 | Yamamoto et al. |
| 5,430,021 A | 7/1995 | Rudnic et al. |
| 5,445,829 A | 8/1995 | Paradissis et al. |
| 5,457,187 A | 10/1995 | Gmeiner et al. |
| 5,462,747 A | 10/1995 | Radebaugh et al. |
| 5,466,446 A | 11/1995 | Stiefel et al. |
| 5,472,708 A | 12/1995 | Chen |
| 5,476,854 A | 12/1995 | Young |
| 5,490,962 A | 2/1996 | Cima et al. |
| 5,508,040 A | 4/1996 | Chen |
| 5,518,680 A | 5/1996 | Cima et al. |
| 5,538,954 A | 7/1996 | Koch et al. |
| 5,543,417 A | 8/1996 | Waldstreicher |
| 5,556,839 A | 9/1996 | Greene et al. |
| 5,567,441 A | 10/1996 | Chen |
| 5,576,022 A | 11/1996 | Yang et al. |
| 5,578,713 A | 11/1996 | McGill, III |
| 5,599,557 A | 2/1997 | Johnson et al. |
| 5,607,685 A | 3/1997 | Cimbollek et al. |
| 5,633,006 A | 5/1997 | Catania et al. |
| 5,672,359 A | 9/1997 | Digenis et al. |
| 5,688,516 A | 11/1997 | Raad et al. |
| 5,702,895 A | 12/1997 | Matsunaga et al. |
| 5,705,190 A | 1/1998 | Broad et al. |
| 5,707,646 A | 1/1998 | Yajima et al. |
| 5,719,132 A | 2/1998 | Lin et al. |
| 5,719,272 A | 2/1998 | Yang et al. |
| 5,725,553 A | 3/1998 | Moenning |
| 5,733,886 A | 3/1998 | Baroody et al. |
| 5,756,473 A | 5/1998 | Liu et al. |
| 5,780,446 A | 7/1998 | Ramu |
| 5,789,584 A | 8/1998 | Christensen et al. |
| 5,808,017 A | 9/1998 | Chang |
| 5,817,321 A | 10/1998 | Alakhov et al. |
| 5,827,531 A | 10/1998 | Morrison et al. |
| 5,837,284 A | 11/1998 | Mehta et al. |
| 5,837,829 A | 11/1998 | Ku |
| 5,840,329 A | 11/1998 | Bai |
| 5,840,760 A | 11/1998 | Carraher, Jr. et al. |
| 5,844,105 A | 12/1998 | Liu et al. |
| 5,849,776 A | 12/1998 | Czemielewski et al. |
| 5,852,180 A | 12/1998 | Patel |
| 5,858,986 A | 1/1999 | Liu et al. |
| 5,864,023 A | 1/1999 | Ku et al. |
| 5,869,170 A | 2/1999 | Cima et al. |
| 5,872,104 A | 2/1999 | Vermeulen et al. |
| 5,872,229 A | 2/1999 | Liu et al. |
| 5,877,243 A | 3/1999 | Sarangapani |
| 5,883,079 A | 3/1999 | Zopf et al. |
| 5,892,008 A | 4/1999 | Ku et al. |
| 5,910,322 A | 6/1999 | Rivett et al. |
| 5,919,219 A | 7/1999 | Knowlton |
| 5,919,489 A | 7/1999 | Saleki-Gerhardt et al. |
| 5,919,916 A | 7/1999 | Gracey et al. |
| 5,929,219 A | 7/1999 | Hill |
| 5,932,710 A | 8/1999 | Liu et al. |
| 5,945,124 A | 8/1999 | Sachs et al. |
| 5,945,405 A | 8/1999 | Spanton et al. |
| 5,962,024 A | 10/1999 | Marvola et al. |
| 5,972,373 A | 10/1999 | Yajima et al. |
| 5,980,942 A | 11/1999 | Katzhendler et al. |
| 5,985,643 A | 11/1999 | Tomasz et al. |
| 5,998,194 A | 12/1999 | Summers, Jr. et al. |
| 6,008,195 A | 12/1999 | Selsted |
| 6,010,718 A | 1/2000 | Al-Razzak et al. |
| 6,013,507 A | 1/2000 | Tomasz et al. |
| 6,027,748 A | 2/2000 | Conte et al. |
| 6,031,093 A | 2/2000 | Cole et al. |
| 6,048,977 A | 4/2000 | Cole et al. |
| 6,051,255 A | 4/2000 | Conley et al. |
| 6,051,703 A | 4/2000 | Cole et al. |
| 6,057,291 A | 5/2000 | Hancock et al. |
| 6,059,816 A | 5/2000 | Moenning |
| 6,063,613 A | 5/2000 | De Lencastre et al. |
| 6,063,917 A | 5/2000 | Ascher et al. |
| 6,068,859 A | 5/2000 | Curatolo et al. |
| 6,110,925 A | 8/2000 | Williams et al. |
| 6,117,843 A | 9/2000 | Baroody et al. |
| 6,120,803 A | 9/2000 | Wong et al. |
| 6,127,349 A | 10/2000 | Chasalow |
| 6,132,768 A | 10/2000 | Sachs et al. |
| 6,132,771 A | 10/2000 | Depui et al. |
| 6,136,587 A | 10/2000 | Tomasz et al. |
| 6,156,507 A | 12/2000 | Hiramatsu et al. |
| 6,159,491 A | 12/2000 | Durrani |
| 6,162,925 A | 12/2000 | Williams et al. |
| 6,183,778 B1 | 2/2001 | Conte et al. |
| 6,187,768 B1 | 2/2001 | Welle et al. |
| 6,214,359 B1 | 4/2001 | Bax |
| 6,218,380 B1 | 4/2001 | Cole et al. |
| 6,228,398 B1 | 5/2001 | Devane et al. |

| | | | | | | |
|---|---|---|---|---|---|---|
| 6,231,875 | B1 | 5/2001 | Sun et al. | 6,723,340 B2 | 4/2004 | Gusler et al. |
| 6,248,363 | B1 | 6/2001 | Patel et al. | 6,723,341 B2 | 4/2004 | Rudnic et al. |
| 6,251,647 | B1 | 6/2001 | De Lencastre et al. | 6,730,320 B2 | 5/2004 | Rudnic et al. |
| 6,265,394 | B1 | 7/2001 | Sterzycki et al. | 6,730,325 B2 | 5/2004 | Devane et al. |
| 6,270,805 | B1 | 8/2001 | Chen et al. | 6,735,470 B2 | 5/2004 | Henley et al. |
| 6,280,771 | B1 | 8/2001 | Monkhouse et al. | 6,740,664 B2 | 5/2004 | Cagle et al. |
| 6,294,199 | B1 | 9/2001 | Conley et al. | 6,746,692 B2 | 6/2004 | Conley et al. |
| 6,294,526 | B1 | 9/2001 | Higuchi et al. | 6,756,057 B2 | 6/2004 | Storm et al. |
| 6,296,873 | B1 | 10/2001 | Katzhendler et al. | 6,767,899 B1 | 7/2004 | Kay et al. |
| 6,297,215 | B1 | 10/2001 | Hancock et al. | 6,777,420 B2 | 8/2004 | Zhi et al. |
| 6,299,903 | B1 | 10/2001 | Rivett et al. | 6,783,773 B1 | 8/2004 | Storm et al. |
| 6,306,436 | B1 | 10/2001 | Chungi et al. | 6,818,407 B2 | 11/2004 | Hancock et al. |
| 6,309,663 | B1 | 10/2001 | Patel et al. | 6,824,792 B2 | 11/2004 | Foreman et al. |
| 6,322,819 | B1 | 11/2001 | Burnside et al. | 6,872,407 B2 | 3/2005 | Notario et al. |
| 6,333,050 | B2 | 12/2001 | Wong et al. | 6,878,386 B1 | 4/2005 | Conley et al. |
| 6,340,475 | B2 | 1/2002 | Shell et al. | 6,878,387 B1 | 4/2005 | Petereit et al. |
| 6,352,720 | B1 | 3/2002 | Martin et al. | 6,906,035 B2 | 6/2005 | Hancock et al. |
| 6,358,525 | B1 | 3/2002 | Guo et al. | 6,929,804 B2 | 8/2005 | Rudnic et al. |
| 6,358,528 | B1 | 3/2002 | Grimmett et al. | 6,946,458 B2 | 9/2005 | Turos |
| 6,383,471 | B1 | 5/2002 | Chen et al. | 6,984,401 B2 | 1/2006 | Rudnic et al. |
| 6,384,081 | B2 | 5/2002 | Berman | 6,991,807 B2 | 1/2006 | Rudnic et al. |
| 6,391,614 | B1 | 5/2002 | Tomasz et al. | 7,008,633 B2 | 3/2006 | Yang et al. |
| 6,399,086 | B1 | 6/2002 | Katzhendler et al. | 7,025,989 B2 | 4/2006 | Rudnic et al. |
| 6,403,569 | B1 | 6/2002 | Achterrath | 2001/0046984 A1 | 11/2001 | Rudnic |
| 6,406,717 | B2 | 6/2002 | Cherukuri | 2001/0048944 A1 | 12/2001 | Rudnic et al. |
| 6,406,880 | B1 | 6/2002 | Thornton | 2002/0004070 A1 | 1/2002 | Rudnic et al. |
| 6,440,462 | B1 | 8/2002 | Raneburger et al. | 2002/0004499 A1 | 1/2002 | Rudnic et al. |
| 6,444,796 | B1 | 9/2002 | Suh et al. | 2002/0015728 A1 | 2/2002 | Payumo et al. |
| 6,468,964 | B1 | 10/2002 | Rowe | 2002/0028920 A1 | 3/2002 | Lifshitz et al. |
| 6,479,496 | B1 | 11/2002 | Wolff | 2002/0042394 A1 | 4/2002 | Hogenkamp et al. |
| 6,495,157 | B1 | 12/2002 | Pena et al. | 2002/0068078 A1 | 6/2002 | Rudnic et al. |
| 6,497,901 | B1 | 12/2002 | Royer | 2002/0068085 A1 | 6/2002 | Rudnic et al. |
| 6,503,709 | B1 | 1/2003 | Bekkaoui et al. | 2002/0081332 A1 | 6/2002 | Rampal et al. |
| 6,506,886 | B1 | 1/2003 | Lee et al. | 2002/0103261 A1 | 8/2002 | Ninkov |
| 6,514,518 | B2 | 2/2003 | Monkhouse et al. | 2002/0106412 A1 | 8/2002 | Rowe et al. |
| 6,515,010 | B1 | 2/2003 | Franchini et al. | 2002/0115624 A1 | 8/2002 | Behar et al. |
| 6,515,116 | B2 | 2/2003 | Suh et al. | 2002/0119168 A1 | 8/2002 | Rudnic et al. |
| 6,530,958 | B1 | 3/2003 | Cima et al. | 2002/0136764 A1 | 9/2002 | Rudnic et al. |
| 6,541,014 | B2 | 4/2003 | Rudnic et al. | 2002/0136765 A1 | 9/2002 | Rudnic et al. |
| 6,544,555 | B2 | 4/2003 | Rudnic et al. | 2002/0136766 A1 | 9/2002 | Rudnic et al. |
| 6,548,084 | B2 | 4/2003 | Leonard et al. | 2002/0150619 A1 | 10/2002 | Rudnic et al. |
| 6,550,955 | B2 | 4/2003 | D'Silva | 2002/0197314 A1 | 12/2002 | Rudnic et al. |
| 6,551,584 | B2 | 4/2003 | Bandyopadhyay et al. | 2003/0012814 A1 | 1/2003 | Rudnic et al. |
| 6,551,616 | B1 | 4/2003 | Notario et al. | 2003/0018295 A1 | 1/2003 | Henley et al. |
| 6,558,699 | B2 | 5/2003 | Venkatesh | 2003/0049311 A1 | 3/2003 | McAllister et al. |
| 6,565,873 | B1 | 5/2003 | Shefer et al. | 2003/0064100 A1 | 4/2003 | Rudnic et al. |
| 6,565,882 | B2 | 5/2003 | Rudnic | 2003/0073647 A1 | 4/2003 | Chao et al. |
| 6,569,463 | B2 | 5/2003 | Patel et al. | 2003/0073648 A1 | 4/2003 | Chao et al. |
| 6,585,997 | B2 | 7/2003 | Moro et al. | 2003/0073826 A1 | 4/2003 | Chao et al. |
| 6,599,884 | B2 | 7/2003 | Avrutov et al. | 2003/0077323 A1* | 4/2003 | Rudnic et al. ................. 424/468 |
| 6,605,069 | B1 | 8/2003 | Albers et al. | 2003/0086969 A1 | 5/2003 | Rudnic et al. |
| 6,605,300 | B1 | 8/2003 | Burnside et al. | 2003/0091627 A1 | 5/2003 | Sharma |
| 6,605,609 | B2 | 8/2003 | Barbachyn et al. | 2003/0096005 A1 | 5/2003 | Rudnic et al. |
| 6,605,751 | B1 | 8/2003 | Gibbins et al. | 2003/0096007 A1 | 5/2003 | Rudnic et al. |
| 6,610,323 | B1 | 8/2003 | Lundberg et al. | 2003/0096008 A1 | 5/2003 | Rudnic et al. |
| 6,610,328 | B2 | 8/2003 | Rudnic et al. | 2003/0099706 A1 | 5/2003 | Rudnic et al. |
| 6,617,436 | B2 | 9/2003 | Avrutov et al. | 2003/0099707 A1 | 5/2003 | Rudnic et al. |
| 6,623,757 | B2 | 9/2003 | Rudnic et al. | 2003/0104054 A1 | 6/2003 | Rudnic et al. |
| 6,623,758 | B2 | 9/2003 | Rudnic et al. | 2003/0104055 A1 | 6/2003 | Rudnic et al. |
| 6,624,292 | B2 | 9/2003 | Lifshitz et al. | 2003/0104056 A1 | 6/2003 | Rudnic et al. |
| 6,627,222 | B2 | 9/2003 | Rudnic et al. | 2003/0104058 A1 | 6/2003 | Rudnic et al. |
| 6,627,223 | B2 | 9/2003 | Percel et al. | 2003/0124196 A1 | 7/2003 | Weinbach et al. |
| 6,627,743 | B1 | 9/2003 | Liu et al. | 2003/0129236 A1 | 7/2003 | Heimlich et al. |
| 6,630,498 | B2 | 10/2003 | Gudipati et al. | 2003/0143268 A1 | 7/2003 | Pryce Lewis et al. |
| 6,632,453 | B2 | 10/2003 | Wassink et al. | 2003/0147953 A1 | 8/2003 | Rudnic et al. |
| 6,635,280 | B2 | 10/2003 | Shell et al. | 2003/0190360 A1 | 10/2003 | Baichwal et al. |
| 6,638,532 | B2 | 10/2003 | Rudnic et al. | 2003/0198677 A1 | 10/2003 | Pryce Lewis et al. |
| 6,642,276 | B2 | 11/2003 | Wadhwa | 2003/0199808 A1 | 10/2003 | Henley et al. |
| 6,663,890 | B2 | 12/2003 | Rudnic et al. | 2003/0203023 A1 | 10/2003 | Rudnic et al. |
| 6,663,891 | B2 | 12/2003 | Rudnic et al. | 2003/0206951 A1 | 11/2003 | Rudnic et al. |
| 6,667,042 | B2 | 12/2003 | Rudnic et al. | 2003/0216555 A1 | 11/2003 | Lifshitz et al. |
| 6,667,057 | B2 | 12/2003 | Rudnic et al. | 2003/0216556 A1 | 11/2003 | Avrutov et al. |
| 6,669,948 | B2 | 12/2003 | Rudnic et al. | 2003/0232082 A1 | 12/2003 | Li et al. |
| 6,669,955 | B2 | 12/2003 | Chungi et al. | 2003/0232089 A1 | 12/2003 | Singh et al. |
| 6,673,369 | B2 | 1/2004 | Rampal et al. | 2003/0235615 A1 | 12/2003 | Rudnic |
| 6,682,759 | B2 | 1/2004 | Lim et al. | 2004/0018234 A1 | 1/2004 | Rudnic et al. |
| 6,696,426 | B2 | 2/2004 | Singh et al. | 2004/0033262 A1 | 2/2004 | Kshirsagar et al. |
| 6,702,803 | B2 | 3/2004 | Kupperblatt et al. | 2004/0043073 A1 | 3/2004 | Chen et al. |
| 6,706,273 | B1 | 3/2004 | Roessler | 2004/0047906 A1 | 3/2004 | Percel et al. |

| | | | |
|---|---|---|---|
| 2004/0048814 | A1 | 3/2004 | Vanderbist et al. |
| 2004/0052842 | A1 | 3/2004 | Rudnic et al. |
| 2004/0058879 | A1 | 3/2004 | Avrutov et al. |
| 2004/0091528 | A1 | 5/2004 | Rogers et al. |
| 2004/0126427 | A1 | 7/2004 | Venkatesh et al. |
| 2004/0126429 | A1 | 7/2004 | Storm et al. |
| 2004/0176737 | A1 | 9/2004 | Henley et al. |
| 2004/0208936 | A1 | 10/2004 | Chorin et al. |
| 2004/0219223 | A1 | 11/2004 | Kunz |
| 2004/0241172 | A1 | 12/2004 | Axworthy et al. |
| 2004/0253249 | A1 | 12/2004 | Rudnic et al. |
| 2004/0265379 | A1 | 12/2004 | Conley et al. |
| 2005/0019401 | A1 | 1/2005 | Burnside et al. |
| 2005/0019402 | A1 | 1/2005 | Burnside et al. |
| 2005/0019403 | A1 | 1/2005 | Burnside et al. |
| 2005/0053658 | A1 | 3/2005 | Venkatesh et al. |
| 2005/0064033 | A1 | 3/2005 | Notario et al. |
| 2005/0064034 | A1 | 3/2005 | Li et al. |
| 2005/0142187 | A1 | 6/2005 | Treacy, Jr. et al. |
| 2005/0163857 | A1 | 7/2005 | Rampal et al. |
| 2005/0203076 | A1 | 9/2005 | Li et al. |
| 2005/0203085 | A1 | 9/2005 | Li et al. |
| 2005/0209210 | A1 | 9/2005 | Ding et al. |
| 2005/0238714 | A1 | 10/2005 | Rudnic et al. |
| 2005/0256096 | A1 | 11/2005 | Combrink et al. |
| 2005/0261262 | A1 | 11/2005 | Ma et al. |
| 2005/0277633 | A1 | 12/2005 | Ma et al. |
| 2006/0003005 | A1 | 1/2006 | Cao et al. |
| 2006/0019985 | A1 | 1/2006 | Ma et al. |
| 2006/0019986 | A1 | 1/2006 | Ding et al. |
| 2006/0110463 | A1 | 5/2006 | Castan et al. |
| 2006/0111302 | A1 | 5/2006 | Romesberg et al. |
| 2006/0194748 | A1* | 8/2006 | Minami et al. ............... 514/29 |
| 2007/0134327 | A1 | 6/2007 | Flanner et al. |
| 2008/0026056 | A1* | 1/2008 | Guimberteau et al. ....... 424/464 |
| 2008/0050430 | A1 | 2/2008 | Flanner et al. |
| 2008/0132478 | A1 | 6/2008 | Flanner et al. |
| 2008/0139526 | A1 | 6/2008 | Treacy et al. |

FOREIGN PATENT DOCUMENTS

| | | |
|---|---|---|
| EP | 0293885 | 12/1988 |
| EP | 0 312 581 | 4/1989 |
| EP | 0436370 | 7/1991 |
| EP | 0652008 | 5/1995 |
| FR | 2585948 | 2/1982 |
| GB | 2087235 | 5/1982 |
| WO | 90/08537 | 8/1990 |
| WO | 94/27557 | 12/1994 |
| WO | 95/20946 | 8/1995 |
| WO | 95/30422 | 11/1995 |
| WO | 96/04908 | 2/1996 |
| WO | 97/22335 | 6/1997 |
| WO | 97/43277 | 11/1997 |
| WO | 98/22091 | 5/1998 |
| WO | 98/46239 | 10/1998 |
| WO | 99/03453 | 1/1999 |
| WO | 99/40097 | 8/1999 |
| WO | 00/49607 | 8/2000 |
| WO | 00/61116 | 10/2000 |
| WO | 01/26663 | 4/2001 |
| WO | 0162229 | 8/2001 |
| WO | 02/38577 | 5/2002 |
| WO | 03/029439 | 4/2003 |
| WO | 03/084517 | 10/2003 |
| WO | WO 2004073695 | * 9/2004 |
| WO | 2005030178 | 4/2005 |
| WO | 2005/056754 | 6/2005 |
| WO | 2005/070941 | 8/2005 |

OTHER PUBLICATIONS

Barry et al, In Vitro Activities of Orally Administered Antimicrobial Agents against Four Species of Bacterial Respiratory Pathogens from U.S. Medical Centers in 1992 and 1993, Antimicrobial Agents and Chemotherapy, 1994, 38(10), 2419-2425.*

Adjei et al., Comparative Pharmacokinetic Study of Continuous Venous Infusion Fluorouracil and Oral Fluorouracil With Eniluracil in Patients with Advanced Solid Tumors, Journal of Clinical Oncology, vol. 20, Issue 6 (Mar. 2002), 1686-19691.

Andes, Pharmacokinetic and Pharmacodynamic Properties of Antimicrobials in the Therapy of Respiratory Tract Infections, Current Opinion in Infectious Diseases, 14(2):165-172, Apr. 2001. (Abstract).

Auckenthaler, Pharmacokinetics and Pharmacodynamics of Oral Beta-Lactam Antibiotics as a Two-Dimensional Approach to Their Efficacy, J Antimicrob Chemother, (2002) 50, 13-17.

Berry et al., Bacteriological Efficacies of Three Macrolides Compared with Those Amoxicillin-Clavulanate Against Streptococcus Pneumoniae Influenzae, Antimicrob Agents Chemother. Dec. 1998: 42(12): 3193-3199.

Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.

Bhargava et al., Pulsed Feeding During Fed-Batch Aspergillus Oryzae Fermentation Leads to Improved Oxygen Mass Transfer, Biotechnol. Prog. 2003, 19, 1091-1094.

Bhargava et al., Pulsed Addition of Limiting-Carbon During Aspergillus Oryzae Fermentation Leads to Improved Productivity of a Recombinant Enzyme, Biotechnology and Bioengineering, vol. 82, No. 1, Apr. 5, 2003, pp. 111-117.

Bishai, Comparative Effectiveness of Different Macrolides: Clarithromycin, Azithromycin, and Erythromycin, Johns Hopkins Point of Care Information Technology (POC-IT), posted Dec. 2001.

Bradley, Staphylococcus Aureus Pneumonia: Emergence of MRSA in the Community, Semin Respir Crit Care Med. 2005; 28(6): 643-649.

Brogden et al., Cefixime. A Review of Its Antibacterial Activity, Pharmacokinetic Properties and Therapeutic Potential, Drugs, Oct. 1989; 38(4): 524-50. (Abstract).

Burgess et al., A Time-Kill Evaluation of Clarithromycin and Azithromycin Against Two Extracellular Pathogens and the Development of Resistance, The Annals of Pharmacotherapy: 1999, vol. 33, No. 12, pp. 1262-1265 (Abstract).

Byfield et al., Relevance of the Pharmacology of Oral Tegafur to its Use as a 5-FU Pro-Drug., Cancer Treat Rep. Jun. 1985; 69 (6): 645-52. (Abstract).

Cappelletty et al., Bactericidal Activities of Cefprozil, Penicillin, Cefaclor, Cefixime, and Loracarbef against Penicillin-Susceptible and Resistant Streptococcus pneumoniae in an In Vitro Pharamcodynamic Infection Model, Antimicrobial Agents and Chemotherapy, May 1996, p. 1148-1152.

Cha et al., Pulsatile Delivery of Amoxicillin Against Streptococcus pneumoniae, Journal of Antimicrobial Chemotherapy, Advance Access Published Oct. 14, 2004.

Craig, Antibiotic Selection Factors and Description of a Hospital-Based Outpatient Antibiotic Therapy Program in the USA, Eur J Clin Microbiol Infect Dis. Jul. 1995; 14(7); 636-42. (Abstract).

Cremieux et al., Ceftriaxone Diffusion into Cardiac Fibrin Vegetation. Qualitative and Quantitative Evaluation by Autoradiography, Fundam Clin Pharmacol. 1991; 5(1);53-60. (Abstract).

Endo et al., Fungicidal Action of Aureobasidin A, a Cyclic Depsipeptide Antifungal Antibiotic, against Saccharomyces cerevisiae, Antimicrobial Agents and Chemotherapy, Mar. 1997, p. 672-676.

Erah et al., The Stability of Amoxycillin, Clarithromycin and Metronidazole in Gastric Juice: Relevance to the Treatment of Helicobacter Pylori Infection, J Antimicrob Chemother Jan. 1997; 39(1):5-12. (Abstract).

Fang, A Study of the Ethical Considerations and Implications, Prozac Weekly and Sarafem in the Wake of Prozac Patent Expiration, 5.22J/10.02J, Biotechnology and Engineering, 2002.

Feder et al. Once-Daily Therapy for Streptococcal Pharyngitis With Amoxicillin, American Academy of Pediatrics, vol. 103(1), Jan. 1999, pp. 47-51.

Freeman et al., The Cyclosporin-Erythromycin Interaction: Impaired First Pass Metabolism in the Pig, Br J Pharmacol. Jul. 1991; 103(3): 1709-12. (Abstract).

Frimodt-Moller, Correlation Between Pharmacokinectic / Pharmacodynamic Parameters and Efficacy for Antibiotics in the Treatment of Urinary Tract Infection, Int. J. Antimicrob. Agents, 19 (2002) 546-53.

Furlanut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2002) 51, 101-106.

Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998; 42(8)1996-2001.

Gnarpe et al., Penicillin Combinations Against Multi-Resistant Urinary Pathogens as an Alternative to Gentamycin Treatment, Microbios 1976: 16(65-66):201-6. (Abstract).

Gordon et al., Rationale for Single and High Dose Treatment Regiments with Azithromycin, Pediatric Infectious Disease Journal. 23(2) Supplement: S102-S107, Feb. 2004. (Abstract).

Goswick et al., Activities of Azithromycin and Amphotericin B Against Naegleria Fowleri in Vitro and in a Mouse Model of Primary Amebic Meningoencephalitis, Antimicrob Agents Chemother. Feb. 2003; 47(2): 524-528.

Harbath et al., Prolonged Antibiotic Prophylaxis After Cardiovascular Surgery and Its Effect on Surgical Site Infections and Antimicrobial Resistance, Circulation Jun. 27, 2000; 101:2916-2921.

Haney, New Drugs Kill Bacteria Resistant to Antibiotics, Called Ketolides, They are Chemically New to the Harmful Bugs, Thursday, Sep. 21, 2000, Seattle Post-Intelligencer.

Harris et al., Esophageal Carcinoma: Curative Treatment, Combined Modalities, The Virtual Hospital, 2004.

Hickey et al., Production of Enterolysin A by a Raw Milk Enterococcal Isolate Exhibiting Multiple Virulence Factors, Microbiology 149 (2003), 655-664.

Hirata et al., Pharmacokinetic Study of S-1, a Novel Oral Fluorouracil Antitumor Drug, Clinical Cancer Research vol. 5, 2000-2005, Aug. 1999.

Hoff et al., Phase I Study with Pharmacokinetics of S-1 on an Oral Daily Schedule for 28 Days in Patients with Solid Tumors, Clinical Cancer Research vol. 9, 134-142, Jan. 2003.

Hoffman et al., Pharmacodynamic and Pharmacokinetic Rationales for the Development of an Oral Controlled-Release Amoxicillin Dosage Form, Journal of Controlled Release 54 (1988) 29-37.

Hoffmann et al., Influence of Macrolide Susceptibility of Efficacies of Clarithromycin and Azithromycin Against Streptococcus Pneumoniae in a Murine Lung Infection Model, Antimicrobial Agents and Chemotherapy, Feb. 2003, p. 739-746, vol. 47, No. 2.

Hyde et al., Macrolide Resistance Among Invasive Streptococcus Penumoniae Isolates, JAMA, Oct. 17, 2001; 286 (15):1857-62. (Abstract).

Iba et al., Comparison Between Continuous Intravenous and Oral Administration of 5-FU with LV, Gan to Kagaku Ryohe. Apr. 1999; 26(5):631-5. (Abstract).

Jacobs, Pharmacodynamic Approach to Antimicrobial Treatment for Respiratory Infections, Department of Pathology, Case Western Reserve University, 2006.

Kaplan et al., Macrolide Therapy of Group A Streptococcal Pharyngitis: 10 Days of Macrolide Therapy (Clarithromycin) is More Effective in Streptococcal Eradication Than 5 Days (Azithromycin), Clin Infect Dis. Jun. 15, 2001; 32 (12):1798-802. Epub May 21, 2001. (Abstract).

Klugman, Bacteriological Evidence of Antibiotic Failure in Pneumococcal Lower Respiratory Tract Infections, Eur Respir J 2002; 20 Suppl. 36, 3s-8s.

Kramar et al., Statistical Optimisation of Diclofenac Sustained Release Pellets Coated with Polymethacrylic Films, Int J Pharm. Apr. 30, 2003; 256(1-2):43-52. (Abstract).

Laine et al., Frequency and Clinical Outcome of Potentially Harmful Drug Metabolic Inteactions in Patients Hospitalized on Internal and Pulmonary Medicine Wards; Focus on Warfarin and Cisapride, Therapeutic Drug Monitoring. 22 (5):503-509, Oct. 2000. (Abstract).

Laine et al., Frequency and Clinical Outcome of Potentially Harmful Drug Metabolic Interactions in Patients Hospitalized on Internal and Pulmonary Medicine Wards: Focus on Warfarin and Cisapride, Therapeutic Drug Monitoring. 22(5):503-509, 2000.

Lamb et al., Ceftriaxone: An Update of its Use in the Management of Community-Acquired and Noscocomial infections, Drugs. 2002;62(7)1041-89. (Abstract).

Lerner-Tung et al., Pharmacokinetics of Intrapericardial Administration of 5-Fluorouracil, Cancer Chemother Pharmacol. 1997; 40(4):318-20. (Abstract).

Lin et al., Multiple-Dose Pharmacokinetics of Ceftibuten in Healthy Volunteers, Antimicrobial Agents and Chemotherapy, Feb. 1995, p. 356-358.

Lindsey et al., Extraction of Antibiotics From Agricultural Wastewater, USGS, 220th ACS Meeting Washington, D.C.; Aug. 20-24, 2000. (Abstract).

Livermore et al., Activity of Ertapenem Against Neisseria Gonorrhoeae, Journal of Antimicrobial Chemotherapy 2004 54(1):280-281.

Lovmar et al., Kinetics of Macrolide Action, The Josamycin and Erythromycin Cases, J. Biol. Chem., vol. 279, Issue 51, 53506-53515, Dec. 17, 2004.

Mainz et al., Pharmacokinetics of Lansoprazole, Amoxicillin and Clarithromycin After Simultaneous and Single Administration, Journal of Antimicrobial Chemotherapy (2002) 50, 699-706.

Eudragit L30D-55. http://eudragit.evonik.com/sites/dc/Downloadcenter/Evonik/Product/EuDRAGIT/Guidelines%20for%20Formulation%20Development%20 and %20Process%20Technology%20for%20Enteric%20Coatings.pdf. Published Mar. 2009, Accessed Aug. 9, 2011.

Aqoat AS-HF. http://signetchem.com/Signet-The-Complete-Excipients-Company-Product-SHIN-ETSU-AQOAT-HPMCAS. Published Dec. 8, 2009. Accessed Aug. 9, 2011.

Lan. Pediatrics vol. 105 No. 2 Feb. 2000.

Pankaj Chhipa et al. /Journal of Pharmacy Research 2009, 2(8), 1404-1408.

Grange et al. Pharmacokinetics of amoxycillin/clavulanate acid in serum and ascitic fluid in cirrhotic patients. Apr. 12, 1989. Abstract only.

Mainz et al. Pharmacokinetics of Iansoprazole, amoxicillin and clarithromycin after simultaneous and single administration. Journal of Antimicrobial Chemotherapy, Jul. 9, 2002, vol. 50, pp. 699-706.

Hilton et al. ("Use of Hydroxypropyl Methylcellulose Acetate Succinate in an Enteric Polymer Matrix to Design Controlled-Release Tablets of Amoxicillin Trihydrate," Journal of pharmaceutical Sciences vol. 82, No. 7, Jul. 1993 pp. 737-743).

Chhipa et al. "Formulation Optimization of Sustained Release Pellets of Itopride Hydrochloride using Different Polymers," Journal of Pharmacy Research 2009 2(8) 1404-1408.

Grange et al. Pharmacokinetics of amoxycillin/clavulanic acid in serum and ascitic fluid in cirrhotic patients. Apr. 12, 1989. Abstract only.

Hilton et al. Use of Hydroxypropyl Methylcellulose Acetate Succinate in an Enteric Polymer Matrix to Design Controlled-Release Tablets of Amoxicillin Trihydrate. Journal of Pharmaceutical Sciences, Jul. 1993, vol. 82, No. 7, pp. 737-743.

Chhipa et al. Formulation Optimization of Sustained Release Pellets of Itopride Hydrochloride using Different Polymers. Journal of Pharmacy Research (2009) 2(8), 1404-1408.

Marten et al., Monthly Report, Jul. 2004, Pulsatile Dosing of Antifungal Compounds, UMBC; to Dr. Robert J. Guttendorf, Advancis Pharmaceutical Corp.

Mazzei et al., How Macrolide Pharmacodynamics Affect Bacterial Killing, Infect Med 6(sE):22-28, 1999. (Abstract).

Nightingale, Pharmacokinectics and Pharmacodynamics of Newer Macrolides, Pediatric Infectious Disease Journal. 16(4):438-443, Apr. 1997. (Abstract).

Olofinlade et al. Anal Carcinoma: A 15-Year Restrospective Analysis, Scand J Gastroenterol 2000:35; 1194-1199.

Pacifico et al., Comparative Efficacy and Safety of 3-Day Azithromycin and 10-Day Penicillin V Treatment of Group A Beta-Hemolytic Streptcoccal Pharyngitis in Children, Antimicrobiol Agents and Chemotherapy, Apr. 1996, 1005-1008, vol. 40, No. 4, (Abstract).

Parmar-Lapasia et al., A Comparison of Two Macrolide Antibiotics in the Treatment of Community-Acquired Iinfections, P & T (Pharmacy & Therapeutics), Oct. 2003. vol. 28, No, 10.

Peters et al., Fluorouracil (5FU) Pharmacokinetics in 5FU Prodrug Formulations with a Dihydropyrimidine Dehydrogenase Inhibitor, Journal of Clinical Oncology, vol. 19, Issue 22 (Nov. 15, 2001): 4267-4269.

Polak, Pharmacokinetics of Amphotericin B and Flucytosine, Postgrad Med J. Sep. 1979; 55(647):667-70. (Abstract).

Porter et al., Antibiotics and Infectious Diseases in Otolaryngology—HNS, Grant Rounds Presentation, UTMB, Dept. of Otolaryngology, May 8, 2002.

Ramminger et al., Transition-Metal Catalyzed Synthesis of Ketoprofen, J. Braz. Chem. Soc. vol. 11, No. 2, 105-111, 2000.

Ramu, Compounds and Methods that Reduce the Risk of Extravasation Injury Associated with the Use of Vesicant Antineoplastic Agents, Baylor College of Medicine, Aug. 6, 1998.

Ranga Rao et al., Influence of Molecular Size and Water Solubility of the Solute on its Release from Swelling and Erosion Controlled Polymeric Matrices, Journal of Controlled Release, 12 (1990) 133-141.

Reza et al., Comparative Evaluation of Plastic, Hydrophobic and Hydrophilic Polymers as Matrices for Controlled- Release Drug Delivery, J. Pharm. Pharmaceut. Sci., 6(2):282-291, 2003.

Richardson, The Discovery and Profile of Fluconazole, J Chemother. Feb. 1990;2(1):51-4 (Abstract) and Houang et al., Fluconazole Levels in Plasma and Vaginal Secretions of Patients After a 150-Milligram Single Oral Dose and Rate of Eradication of Infection in Vaginal Candidiasis, Antimicrob Agents Chemother, May 1990; 34(5):909-10. (Abstract).

Rivkees et al., Dexamethasone Treatment of Virilizing Congenital Adrenal Hyperplasia: The Ability to Achieve Normal Growth, Pediatrics 2000; 106; 767-773.

Roblin et al., In Vitro Activity of a New Ketolide Antibiotic; HMR 3647, Against Chlamydia Pneumoniae, Antimicrob Agents Chemother. Jun. 1998; 42(6): 1515-15116.

Santini et al. The Potential of Amifostine: From Cytoprotectant to Therapeutic Agent, Haematologica Nov. 1999; 84(ii): 1035-1042.

Sanz et a., Cefepime Plus Amikacin Versus Piperacillin-Tazobactam Plus Amikacin for Initial Antibiotic Therapy in Hematology Patients with Febrile Neutropenia: Results of an Open, Randomized, Multicentre Trial, Journal of Antimicrobial Chemotherapy (2002) 50, 79-88.

Schaad et al., Azithromycin Versus Penicillin V for Treatment of Acute Group A Streptococcal Pharyngitis, The Pediatric Infectious Disease Journal: vol. 21(4) Apr. 2002, pp. 304-308.

Schweizer et al., "Single Shot" Prevention in Abdominal Surgery. Antibiotics with Long Half-Life (Cefriazone, Omidazole) vs. Antibiotics with Short Half-Life (Cefazolin, Metronidazole, Clindamycin), Helv Chir Acta. Apr. 1994; 60 (4):483-8. (Abstract).

Shvartzman et al., Treatment of Streptococcal Pharyngitis with Amoxycillin Once a Day, BMJ vol. 306, pp. 1170-1172, May 1, 1993.

Stringer et al., Section 3: Diseases of the Ear, Part 4: Inner Ear, Chapter 46: Ototoxicity, Paparella: vol. II, Otology and Neuro-Otology, W B. Saunders Co., 3rd Edition, 1990.

Suda et al., The Synthesis and In Vitro and In Vivo Stability of 5-Fluorouracil Prodrugs Which Possess Serum Albumin binding Potency, Biol Pharm Bull. Sep. 1993;16(9):876-7. (Abstract).

Sandip et al., Controlled Release Formulation of Tramadol Hydrochloride Using Hydrophilic and Hydrophobic Matrix System, AAPS PharmSciTech 2003; 4(3) Article 31.

Todar's Online Textbook of Bacteriology, Antimicrobial Agents Used in Treatment of Infectious Disease 2002 Kenneth Totter University of Wisconsin-Madison Department of Bacteriology.

Vanderkooi et al., Antimicrobial Resistance and the Pneumococcus, Infectious Diseases and Microbiology, vol. 3, Issue 5, May 2004.

Villalobos et al., Pharmacokinetics and Pharmacodynamics of Antibacterial Agents in Pediatrics: A Practical Approach, Jacksonville Medicine, Aug. 1998.

Waters, Colorectal Cancer-Drug Treatment, Hospital Pharmacist, vol. 11, pp. 17-192, May 2004.

Wattenberg, Prevention of Carcinogenesis of the Respiratory Tract by Chemopreventive Agents Delivered by Aerosol, International Society of Cancer Chemoprevention, vol. 1, No. 6, Jan. 2003.

Whitehead et al., Amoxycillin Release From a Floating Dosage Form Based on Alginates, International Journal of Pharmaceutics 210 (2000) 45-49.

Yousef et al., Combined Action of Amoxycillin and Dicloxacillin Against Staphylococcus Aureus In Vitro, Pharmazie Sep. 1985; 40(9):650-1. (Abstract).

About Macrolides, About That Bug.com (2006).

Acepromazine Maleate, DRUGS.

Allergy Site Navigator, Drug Classification A-D, 2012.

Amoxycillin (As Trihydrate), Moxyvit (2003).

Amoxicillin + Clavulanate, PetPlace.com (2005).

Answers.com, Macrolide (2006).

Antimetabolites, GPnotebook (2005).

Augmentin, Product Information, GlaxoSmithKline, Physicians Desk References, Jun. 2004, pp. 1421-1433.

Augmentin XR (PDR entry for) (GlaxoSmithKline), (Amoxicillin/Clavulanate Potassium), Extended Release Tablets, Jun. 2004.

Beta Lactem Antibiotics, Health 24.com (2005).

Biaxin XL, Once-Daily Biaxin XL. Clarithromycin Extended-Release Tablets, Abbott Laboratories Online (2004).

Biaxin XL, Once-daily, Clarithromycin Extended-Release Tablets (2005).

Biaxin, Dosage and Adminstration, 2012.

Biaxin Filmtab, Biaxin XL Filmtab, Biaxin Granules, pp. 1-25, Abbott Laboratories (2005).

Body Chemistry, Acid Alkaline Foods, Acid Reflux? Gas, Acid Indigestion, Acid/Alkaline Balance, Printed from timberware.com/chemistry.html on Jan. 2, 2012.

Carers of Crohns, Antibiotics, 2012.

Citizen Petition, McNeil Consumer & Specialty Pharmaceuticals, Mar. 19, 2004.

Clarithromycin Extended-Release Scientific Posters Presented to the 39th Interscience Conference on Antimicrobial Agents and Chemotherapy (ICAAC). San Francisco, Sep. 26-29, 1999.

Clearance and the Elimination Rate Constant, Ke (Elimination Rate)—Half-Life, Oct. 14, 2002.

Complementary Medicine Saves Money, Medicine, Greenhealthwatch.com, Collection of medical headlines citing to sources dated between May 1, 1997 and Aug. 10, 2002.

Cross-Reference Art Collections, 907-907, USPTO.gov, 2012.

Declaration of Michael J. Rybak from the prosecution history of U.S. Appl. No. 09/792,092, filed Sep. 23, 2002.

Dispensing Errors With Depakote, New Formulation Creates Confusion, Patient Safety, Practitioners Reporting News, USP Issued Mar. 3, 2001.

Drugs.com, Drug Information for Diclofenac (Topical) (2006).

Drug, Bio-Affecting and Body Treating Compositions, 475 Sustained or differential release, United States Patent and Trademark Office, Classification Definitions as of Jun. 30, 2000.

Elimination Rate Constant/Half-Life, Ke (Elimination Rate)—Half-Life, Oct. 14, 2002.

Emulsions, Secundum Artem, vol. 4, No. 1, printed from www.padocklabs.com/html/resource/pdf/sed Artem 4.1.pdf on Jan. 2, 2012.

Encyclopedia Britannica Online, Types of Drugs>Antimicrobial Drugs>Antibiotics>Macrolides, Mar. 28, 2006.

Excenel, Swine Health Management, Prewean Program. Pfizer Salud Animal (2005).

Fabrication of Metronidazole Strips, 996 Die Pharmazie 50(1995) February, No. 2.

Five vs. 10 Days of Therapy for Streptococcal Pharyngitis, American Family Physician, Feb. 15, 2001.

Food and Drug Administration Center for Drug Evaluation and Research Approved Drug Products With Therapeutic Equivalence Evaluations, 24th Edition, Feb. 26, 2004.

Getting a Drug into the Body: Absorption, from How Drugs Work: Basic Pharmacology for Healthcare Professionals, Hugh McGarock, 2nd Edition, May 2005.

Highlights on Antineoplastic Drugs, Pharmacia, vol. 11, No. 4, 1993.

Jock Itch and Other dermatophytes. Mycolog.com (Sep. 2002).

Klarithran, Ranbaxy(SA)(PTY) LTD, Jun. 2005.

Klucel Hydroxypropylcellulose (HPC). Hercules Incorporated (2004).

MedicineNet.com, Generic Name: Acyclovir, Brand Name: Zovirax, Dec. 31, 1997.

Meeting the Challenge of a New Generation of Respiratory Pathogens, MAC (2001).

The Merck Index, An Encyclopedia of Chemicals, Drugs, and Biologicals, Twelfth Edition, pp. 397-398 (1996).

Methods of Formulation Controlled Release Products Outside of the Claims of Forest Laboratory Patents U.S. 4,369,172 and U.S. 4,389,393, Technical Information Dow Chemical Feb. 1991.

Miconazole, The Merck Index Results-Form view, Monograph No. 06202 (2005).

Mode of Action of Macrolides in Blocking Translation During Bacterial Protein Synthesis: Blocking Peptidyltransferase. Doc Kaiser's Microbiology Home Page, Oct. 13, 2004.

Module 8—Therapeutics. May 25, 2002, Newcastle. BPAIIG Immunology/Infectious Diseases Training Programme, Module: Therapeutics.

Monistat, Which Treatment is Right for You?, Vaginal vs. Oral Therapy (2004).

Neisseria Meningitidis, The Doctor's Doctor, Nov. 8, 2004.

New-Generation Aromatase Inhibitor for Breast Cancer: Anastrozole Challenges Tamoxifen in First-Line Therapy, 10th European Cancer Conference (ECCO 10), Vienna, Austria/Sep. 12-16, 1999.

New Product Newswire, Drug Topics Archive, Aug. 5, 2002.

Nitrofurantoin, Eckerd Prescription Advisory, Feb. 15, 2001.

Nursing, Cancer Nursing: Principles and Practice, Fifth Edition, Jones and Barlett Publishers, 2000.

Oral Capecitabine Should Improve Convenience of Chemoradiation for Locally Advanced Rectal Cancer—New Treatment Appears to be Safe and Effective, PeerView Press, Chemotherapy (ICAAC), Sep. 27-30, 2002; San Diego, CA, 40th Annual Meeting of Infectious Diseases Society.

Oral Extended (Controlled) Release Dosage Forms, In Vivo Bioequivalence and In Vitro Dissolution Testing, Office of Generic Drugs (1993).

Pharmaceuticals, Pharmacos Unit F2 Pharmaceuticals V 6.0, Eudralex Collection 3AQ19a 1992.

Physicians Desk Reference, PDR 57 Edition 2003, p. 402/Abbott.

Principles of Diagnosis of Infectious Diseases and Antimicrobial Therapy, Antibiotic Guideline, Dr. Norman Miller et al., 2nd Edition, Chapters 1-3, printed from www.sassit.co.za/Journal/Infections/Antibiotics/Middes/AntibioticGuide/pdf printed on Jan. 2, 2012.

Procardia XL (Nifedipine) Extended Release Tablets for Oral Use, 69-4467-00-8, Pfizer Labs, Aug. 2003.

Summary of Product Characteristics, Doxycycline Capsules BP 50mg, Nov. 2001.

Sustained or Differential Release Type, USPTO Classification Definitions (Dec. 2002 Edition) 964.

Sustained-Release Dosage Forms, Degussa, Rohm Pharma Polymers, printed from www.solimide, eu/en/pharmapolymers/service/literature/practical_course.Par.0001.TROW.0010.Tcell.0003.File, tmp/pc_30_sustained.pdf on Jan. 2, 2012.

Testicular Cancer: Questions and Answers, Cancer Facts, National Cancer Institute, Aug. 14, 2003.

Traditional Chemotherapy, Chapter 25 from Prevention and Therapy of Cancer and Other Common Disease: Alternative and Traditional Approaches; Infomedix 1996.

Bahnmuller, Metabolites of Microorganisms. 248. Synthetic Analogs of Saphenamycin, J. Antibiot. (Tokyo). Nov. 1988; 41(11): 1552-60.

Borman, Chemistry Highlights 2005, Chemical & Engineering News, Dec. 19, 2005, vol. 83, No. 51, pp. 15-20.

Bradley, Staphylococcus Aureus Pneumonia: Emergence of MRSA in the Community, Semina Respir Crit Care Med. 2005; 26(6): 643-649.

Cirz. et al., Inhibition of Mutation and Combating the Evolution of Antibiotic Resistance, PLOS Biology, Jun. 2005, vol. 3, Issue 6, e176, pp. 1024-1033.

Darst, New Inhibitors Targeting Bacterial RNA Polymerase, TRENDS in Biochemical Sciences, vol. 29, No. 4, Apr. 2004, pp. 159-162.

Dellit, M.D., Tim, University of Washington and Infectious Diseases Society of Washington: Jeffrey Duchin, MD, Public Health-Seattle & King County and University of Washington; Jo Hofmann, MD, Washington State Department of Health and University of of Washington; Erika Gumai Olson, MD, Tacome-Pierce County Health DepartmentAntibiotic Resistance Task Force, Interim Guidelines for Evaluation and Management of Community-Associated Methicillin-Resistant Staphylococcus Aureus Skin and Soft Tissue Infections in Outpatient Settings, Sep. 2, 2004.

Geiger et al., Metabolites of Microorganisms. 247, Phenazines from Streptomyces Antibioticus, Strain Tu 2706, J Antibiot (Tokyo). Nov. 1988; 41(11): 1542-51.

Gorwitz et al., Strategies for Clinical Management of MRSA in the Community; Summary of an Expert's Meeting Convened by the Centers for Disease Control and Prevention, Department of Health and Human Services Centers for Disease Control and Prevention, Mar. 2006.

Henry, Disabling Resistance Inhibiting Key Protease Prevents Bacteria From Evolving Drug Resistance, Chemical and Engineering News, May 16, 2005, vol. 83, No. 20, p. 8.

Johnson, N. J. Experts Urge Prudent Antibiotic Use, Examiner.Com, The Associated Press, Jul. 31, 2006.

Kitahara et al., Saphenamycin, A Novel Antibiotic From a Strain of Streptomyces, J Antibiot (Tokyo). Oct. 1982; 35 (10): 1412-4.

Laursen et al., Solid-Phase Synthesis of New Saphenamycin Analogues with Antimicrobial Activity, Bioorg. Med. Chem. Lett. Jan. 21, 2002: 12(2): 171-5.

Laursen et al., First Synthesis of Racemic Saphenamycin and Its Enantiomers. Investigation of Biological Activity, Bioorg. Med. Chem. Mar. 6, 2003: 11(5): 723-31.

Laursen et al., Efficient Synthesis of Glycosylated Phenazine Natural Products and Analogs with DISAL (Methyl 3, 5-Dinitrosalicylate) Glycosyl Donors, Org. Biomol. Chem, Sep. 21, 2003; 1(18): 3147-53.

Reusser, Inhibition of Ribosomal and RNA Polymerase Functions by Rubradirin and Its Aglycone, J Antibiot (Tokyo) Nov. 1979; 32(11): 1186-92.

Rihn, et al., Community-Acquired Methicillin-Resistant Staphylococcus Aureus: An Emerging Problem in the Athletic Population, AM J Sports Med. Dec. 2005; 33(12): 1924-9.

Salmenlinna et al., Community-Acquired Methicillin-Resistant Staphylococcus aureus, Finland, Emerg, Infect. Dis, Jun. 2002, 8(6): 602-7.

Vandenesch et al., Community-Acquired Methicillin-Resistant Staphylococcus aureus Carrying Panton-Valentine Leukocidin Genes: Worldwide Emergence, Emerg. Infect. Dis, Aug. 2003; 9(8): 978-84.

Can We Prevent Bacteria From Developing Resistance to Antibiotics?, Sep. 2005, AAPS News Magazine 15.

Healthcare-Associated Methicillin Resistant Staphylococcus aureus (HA-MRSA), Department of Health and Human Services, Centers for Disease Control and Prevention, Jun. 1, 2005.

Methicillin-Resistant Staphylococcus aureus, HealthLink, Medical College of Wisconsin, Information Provided by the Wisconsin Department of Health and Human Services, Article Reviewed: Apr. 10, 2004, 2003 Medical College of Wisconsin.

Methicillin-Resistant Staphylococcus aureus (MRSA) Infection, Written by Dr. Alan Johnson, Clinical Scientist, Webiste: www.mrsasupport.co.uk, Jan. 8, 2005.

The Public's Health, Back-To-School: Review Immunization Records Early, What Doctors and Parents Need to Know About Immunizations and School, vol. 5, No. 7, Jul.-Aug. 2005.

Sulfenamide Class Antibiotics, ChemicalLand21.com, 2012.

Craig, "Pharmacokinetic/Pharmacodynamic Parameters: Rationale for Antibacterial Dosing of Mice and Men", Clinical Infectious Diseases, Jan. 1998, vol. 26, pp. 1-12.

* cited by examiner

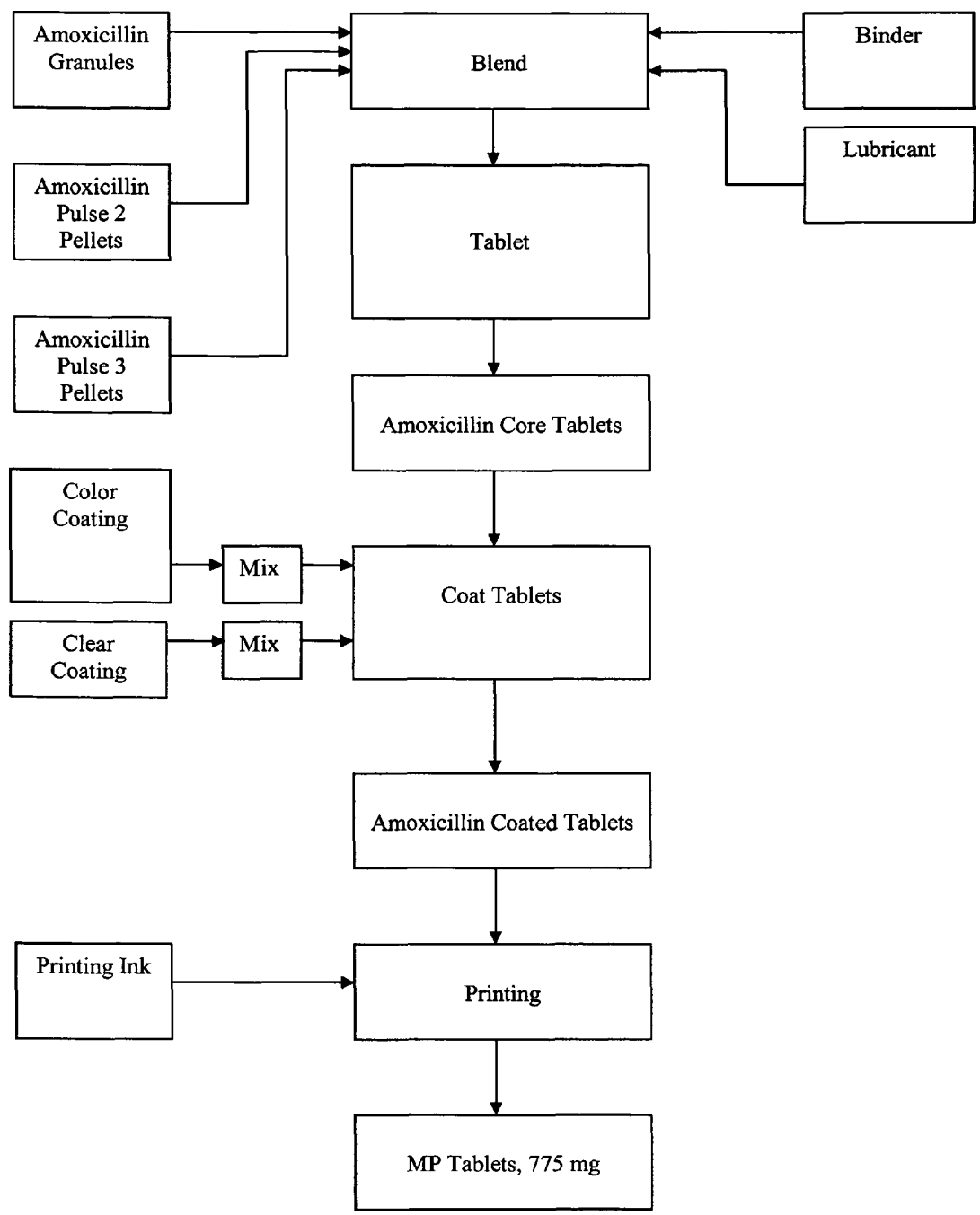

COMPOSITIONS AND METHODS FOR IMPROVED EFFICACY OF PENICILLIN-TYPE ANTIBIOTICS

This application claims the priority of U.S. Provisional Application Ser. No. 60/748,660 filed on Dec. 8, 2005, the disclosures of which are hereby incorporated by reference in their entireties.

This invention relates to an antibiotic product, to its formulation, and to its use in treating bacterial infections. Particularly, this invention relates to an antibiotic product that contains a penicillin-type antibiotic, as well as to the product's formulation and to its use in treating bacterial infections, wherein the infecting pathogen has an $MIC_{90} \geq 0.06$ µg/mL. for the penicillin-type antibiotic used. More particularly, this invention relates to such an antibiotic product that contains a beta-lactam antibiotic, as well as to the product's formulation and to its use in treating bacterial infections. Still more particularly, this invention relates to such a product that contains amoxicillin, to the product's formulation, and to the product's use in treating bacterial infections.

In accordance with an aspect of the invention there is provided a once-a-day penicillin-type antibiotic product for treating a bacterial infection in a patient or subject, comprising a penicillin-type antibiotic composition.

In accordance with a further aspect of the invention the penicillin-type antibiotic composition comprises at least one dosage form, which dosage form comprises at least one penicillin-type antibiotic and a pharmaceutically acceptable carrier. The dosage form(s) is/are formulated such that when the penicillin-type antibiotic composition is administered to a patient or subject in need thereof, the composition provides (or maintains) a concentration of the given penicillin-type antibiotic in the serum at or above the $MIC_{90}$ for an infecting bacterial pathogen for at least 5 hours within a 24-hour dosing interval. The dosage form(s) is/are further formulated such that the penicillin-type antibiotic composition provides (and preferably maintains) a serum concentration of the given penicillin-type antibiotic that is $\geq 0.06$ µg/mL., and such that the penicillin-type antibiotic composition contains the total dosage of the given penicillin-type antibiotic for a 24-hour dosing interval.

In a further aspect, the once-a-day pharmaceutical formulation providing a daily dosage of penicillin-type antibiotic such as to provide (or maintain) a serum concentration of penicillin-type antibiotic in a patient or subject at or above a bacterial pathogen's drug-specific $MIC_{90}$ for at least five hours (preferably for at least five consecutive hours) of a 24-hour dosing interval, comprises a modified release dosage form(s) or an immediate release dosage form(s) in combination with a modified release dosage form(s), with such modified release dosage form(s) being: a delayed release dosage form(s), a sustained (or extended) release dosage form(s), and/or combinations of the forgoing. Such sustained (or extended) release dosage forms may be formulated so that initiation of release of the penicillin-type antibiotic therefrom is not substantially delayed after administration of the penicillin-type antibiotic composition or it may be formulated so that initiation of release of the penicillin-type antibiotic therefrom is substantially delayed after administration of the penicillin-type antibiotic composition.

In accordance with a still further aspect of the invention the penicillin-type antibiotic composition may be labeled for use. Such labeling for use may comprise directives conveyed in any tangible or verbal medium of expression to administer the composition once-a-day to a patient or subject in need thereof, to treat an indication known, or suspected, to be caused by a bacterial pathogen, known, or suspected, to have an $MIC_{90} \geq 0.06$ µg/mL. for the penicillin-type antibiotic used. As non-limiting examples of the forms in which and/or on which the labeling for use of the penicillin-type antibiotic composition may be expressed there may be mentioned: prescriptions; protocols; labels; packaging; packaging inserts; coatings; embossings; scorings; trademarks and/or tradedress, or portions thereof, such as by way of marks and/or dress, or portions thereof, denoting daily, once-a-day, one-a-day, 24-hour, and like marks and/or like dress, or portions thereof; imprinted blister packets; capsule shells; and combinations of the foregoing.

In a preferred embodiment of the once-a-day product the penicillin-type antibiotic composition is formulated so as to maintain a concentration of the penicillin-type antibiotic in the serum of the patient or subject at or above the $MIC_{90}$ of the infecting bacterial pathogen for that penicillin-type antibiotic for at least five consecutive hours out of a 24-hour dosing interval.

As referred to herein, and as is known in the art, the term "$MIC_{90}$" refers to the minimum concentration of a specific antibiotic that is required to inhibit the growth of ninety percent (90%) of the strains of a specific microorganism (bacterial pathogen) species.

As referred to herein, and as is known in the art, the term "penicillin-type antibiotic" generally and broadly refers to an antibiotic from the penicillin class of antibiotics, and shall include beta-lactams, such as amoxicillin.

After administration to a subject, the concentration of antibiotic may be measured in whole blood or plasma obtained from the subject. As known in the art, such measured antibiotic concentration includes antibiotic bound to serum proteins. As known in the art, unbound antibiotic concentration may be determined by use of a correction factor based on known or measured binding of the antibiotic to serum proteins.

In the treatment of bacterial infections, penicillin-type antibiotics, such as beta-lactams, are generally dosed in formulations that require multiple administrations over the course of any given 24-hour period. As is known in the art, such dosing regimens may be twice-a-day (b.i.d.), whereby the composition is administered every 12 hours; three times daily (t.i.d.), whereby the composition is administered every 8 hours; four times daily (q.i.d.), whereby the composition is administered every 6 hours; or such dosing regimens may even conceive of dosing the composition in excess of four administrations per day. Repeated administrations of a drug throughout a 24-hour period may be disruptive to meals or sleep, thereby presenting a significant inconvenience for patients. In the treatment of elderly or incapacitated patients multiple administration regimens can result in poor compliance, and hence an ineffective treatment of the infection. Existing immediate release and modified release amoxicillin formulations are designed and intended to be administered at least twice-a-day or more, to thereby prolong delivery of the drug throughout the duration of a 24-hour period. Some of these formulations contain relatively high doses of amoxicillin that can exacerbate untoward gastrointestinal side effects, including nausea and diarrhea.

Accordingly, there is a need in the art for effective once-a-day compositions and regimens, that would allow for less frequent dosing, but would neither compromise the effectiveness of the given antibiotic, nor require such a high dosage thereof as would exacerbate side effects or multiply production costs.

In one aspect the present invention provides for a once-a-day pharmaceutical formulation providing a daily dosage of penicillin-type antibiotic, such as to provide a serum concentration of penicillin-type antibiotic in a patient or subject at or above an infecting bacterial pathogen's drug-specific $MIC_{90}$ for at least five hours within the 24-hour period following administration.

In a preferred aspect the present invention provides for a once-a-day pharmaceutical formulation providing a daily dosage of penicillin-type antibiotic, such as to maintain a serum concentration of penicillin-type antibiotic in a patient or subject at or above an infecting bacterial pathogen's drug-specific $MIC_{90}$ for at least five consecutive hours within the 24-hour period following administration.

More specifically, in accordance with one aspect of the invention there is provided a once-a-day penicillin-type antibiotic composition comprising at least one dosage form that contains a penicillin-type antibiotic and a pharmaceutically acceptable carrier. In a further aspect of the invention the once-a-day penicillin-type antibiotic composition is formulated so that when administered to a patient, or to subject, it provides a T>$MIC_{90}$ in the serum for at least 5 hours within the 24-hour period following administration. In a still further aspect of the invention the serum concentration that is provided for at least 5 hours is one that is $\geqq 0.06$ μg/mL. In a yet still further aspect of the invention the once-a-day penicillin-type antibiotic composition contains the total dosage of the penicillin-type antibiotic for a twenty-four hour dosing interval.

Preferably, in one aspect of the invention there is provided a once-a-day penicillin-type antibiotic composition comprising at least one dosage form that contains a penicillin-type antibiotic and a pharmaceutically acceptable carrier. In a further preferred aspect of the invention the once-a-day penicillin-type antibiotic composition is formulated so that when administered to a patient, or to a subject, it maintains a T>$MIC_{90}$ in the serum for at least 5 consecutive hours within the 24-hour period following administration. In a still further preferred aspect of the invention the serum concentration that is maintained for at least 5 consecutive hours is one that is $\geqq 0.06$ μg/mL. In a yet still further preferred aspect of the invention the once-a-day penicillin-type antibiotic composition contains the total dosage of the penicillin-type antibiotic for a twenty-four dosing interval.

In one once-a-day embodiment, the composition provides a serum concentration of penicillin-type antibiotic in a patient or subject that is at least equivalent to the drug-specific $MIC_{90}$ of the bacterial pathogen causing the infection in the patient or subject, for at least five hours within the 24-hour period following administration.

In another once-a-day embodiment, the composition maintains a serum concentration of penicillin-type antibiotic in a patient or subject that is at least equivalent to the drug-specific $MIC_{90}$ of the bacterial pathogen causing the infection in the patient or subject, for at least five consecutive hours within the 24-hour period following administration.

In one embodiment the composition provides a serum concentration of penicillin-type antibiotic in a patient or subject at or above a given bacterial pathogen's drug-specific $MIC_{90}$ for at least five hours within the 24-hour period following administration. In another embodiment the composition provides a serum concentration of penicillin-type antibiotic in a patient or subject at or above a given bacterial pathogen's $MIC_{90}$ for at least six hours within the 24-hour period following administration. In another embodiment the composition provides a serum concentration of penicillin-type antibiotic in a patient or subject at or above a given bacterial pathogen's $MIC_{90}$ for at least eight hours within the 24-hour period following administration. In another embodiment the composition provides a serum concentration of penicillin-type antibiotic in a patient or subject at or above a given bacterial pathogen's $MIC_{90}$ for at least nine hours within the 24-hour period following administration. Generally, the composition does not provide a serum concentration of penicillin-type antibiotic in a patient or subject at or above a given bacterial pathogen's $MIC_{90}$ for more than nine hours within the 24-hour period following administration.

In one embodiment the composition maintains a serum concentration of penicillin-type antibiotic in a patient or subject at or above a given bacterial pathogen's drug-specific $MIC_{90}$ for at least five consecutive hours within the 24-hour period following administration. In another embodiment the composition maintains a serum concentration of penicillin-type antibiotic in a patient or subject at or above a given bacterial pathogen's $MIC_{90}$ for at least six consecutive hours within the 24-hour period following administration. In another embodiment the composition maintains a serum concentration of penicillin-type antibiotic in a patient or subject at or above a given bacterial pathogen's $MIC_{90}$ for at least eight consecutive hours within the 24-hour period following administration. In another embodiment the composition maintains a serum concentration of penicillin-type antibiotic in a patient or subject at or above a given bacterial pathogen's $MIC_{90}$ for at least nine consecutive hours within the 24-hour period following administration. Generally, the composition does not maintain a serum concentration of penicillin-type antibiotic in a patient or subject at or above a given bacterial pathogen's $MIC_{90}$ for more than nine consecutive hours within the 24-hour period following administration.

In particularly preferred embodiments the penicillin-type antibiotic is amoxicillin.

Generally, the daily dosage of penicillin-type antibiotic will depend on various factors such as the bacterial pathogen to be targeted, the known resistance or susceptibility of the bacterial pathogen to the given penicillin-type antibiotic, and the known $MIC_{90}$ of the given bacterial pathogen for the given penicillin-type antibiotic.

Generally, the daily dosage of amoxicillin used in the invention comprises from about 250 to about 3000 mg. Preferably the daily dosage of amoxicillin used in the invention comprises from about 500 to about 2500 mg. More preferably the daily dosage of amoxicillin used in the invention comprises from about 775 to about 1550 mg.

In an embodiment the daily dosage of amoxicillin is 775 mg.

In a further aspect, the present invention provides a method of treating various indications in a patient, or in a subject, caused by bacterial pathogens, which treating comprises administering to the patient, or to the subject, once-a-day the herein-above described and herein-below described penicillin-type antibiotic compositions. As non-limiting examples of the indications for which the herein-above described and herein-below described penicillin-type antibiotic compositions may be used to treat a patient there may be mentioned: pharyngitis, tonsillitis, sinusitis, bronchitis, pneumoniae, ear infection (otitis media), uncomplicated skin and skin structure infections, and uncomplicated urinary infections.

In a further aspect, the present invention provides a method of treating infection in a patient or subject caused by bacterial pathogens, comprising administering to the patient or subject once-a-day the herein-above described and herein-below described penicillin-type antibiotic compositions so as to maintain a serum concentration of penicillin-type antibiotic in a patient or subject at or above a given bacterial pathogen's drug-specific $MIC_{90}$ for at least five hours (preferably for at least five consecutive hours) of a 24-hour dosing interval. As non-limiting examples of the infectious bacterial pathogens against which the herein-above described and herein-below described penicillin-type antibiotic compositions may be used there may be mentioned Aerobic Gram-positive microorganisms such as *Staphylococcus aureus, Streptococcus pneumoniae, Streptococcus pyogenes, Streptococcus agalactiae, Streptococci* (Groups C, F, G), and *Viridans* group streptococci; Aerobic Gram-negative microorganisms such as *Haemophilus influenzae, Haemophilus parainfluenzae, Moraxella catarrhalis, Bordetella pertussi, Legionalla pneumophila, Pasteurella multocida* and *Klebsiella pneumoniae*; Anaerobic Gram-positive microorganisms such as *Clostridium perfringens, Peptococcus niger*, and *Propionibacterium acnes*; Anaerobic Gram-negative microorganisms such as *Prevetolla melaninogenica* (formerly *Bacterocides melaninogenicus*); *Mycoplasma pneumoniae; Chlamydia pneumoniae; Mycobacterium avium* complex (MAC) consisting of *Mycobacterium avium* and/or *Mycobacterium intracellulare; Helicobacter pylori; Bacterocides fragilis; Fusobacterium nucleatum; Peptostreptococcus magnus; Peptostreptococcus micros*; and *Escherichia coli*.

It will be appreciated by those of ordinary skill in the art that the methods and formulations hereinabove described and hereinbelow described for the penicillin-type antibiotic amoxicillin, or for other beta-lactam antibiotics, are also applicable to amoxicillin, or to other beta-lactam antibiotics, in combination with clavulanate, or in combination with other beta-lactamase inhibitors, particularly for treating infections where beta-lactamase producing pathogens are implicated.

In a further aspect, the once-a-day pharmaceutical formulation providing a daily dosage of penicillin-type antibiotic such as to provide (or maintain) a serum concentration of penicillin-type antibiotic in a patient or subject at or above a bacterial pathogen's drug-specific $MIC_{90}$ for at least five hours (preferably for at least five consecutive hours) of a 24-hour dosing interval, may comprise a modified release dosage form(s) or an immediate release dosage form(s) in combination with a modified release dosage form(s), with such modified release dosage form(s) being: a delayed release dosage form(s), a sustained (or extended) release dosage form(s), and/or combinations of the forgoing. The formulating of such dosage forms will be apparent to those of skill in the art in view of the disclosures herein further guided by the disclosures of U.S. patent application Ser. Nos. 10/894,787; 10/894,786; 10/894,994; 10/917,059; 10/922,412; and 10/940,265; and by the disclosures of U.S. Pat. Nos. 6,544,555; 6,623,757; and 6,669,948; all of which are hereby incorporated by this reference in their entireties.

In one preferred embodiment the once-a-day pharmaceutical formulation providing a daily dosage of penicillin-type antibiotic, such as to provide (or maintain) a serum concentration of penicillin-type antibiotic in a patient or subject at or above a bacterial pathogen's drug-specific $MIC_{90}$ for at least five hours, (preferably for at least five consecutive hours) of a 24-hour dosing interval, comprises a sustained (or extended) release dosage form(s). In this embodiment the sustained (or extended) release dosage form(s) is designed and intended to release the penicillin-type antibiotic slowly over time, such as to maintain a serum concentration of penicillin-type antibiotic in a patient or subject at or above a bacterial pathogen's drug-specific $MIC_{90}$ for at least five consecutive hours.

In a preferred embodiment, the penicillin-type antibiotic composition is a once a day composition, whereby after administration of the penicillin-type antibiotic composition, no further composition is administered during the day; i.e., the preferred regimen is that the composition is administered only once over a twenty-four hour period. Thus, in accordance with the present invention, there is a single administration of a penicillin-type antibiotic composition formulated so as to provide (or maintain) a serum concentration of penicillin-type antibiotic in a patient or subject at or above a bacterial pathogen's drug-specific $MIC_{90}$ for at least five hours (preferably for at least five consecutive hours) within the 24-hour period following administration. The term single administration means that the total penicillin-type antibiotic administered over a twenty-four hour period is administered at the same time, which can be a single tablet or capsule or two or more thereof, provided that they are administered at essentially the same time.

While the hereinabove described and hereinbelow described compositions may be used to improve the efficacy of any penicillin-type antibiotic, they are particularly useful for improving the efficacy of antibiotics that include a beta-lactam ring or a portion thereof, as non-limiting examples of such antibiotics there may be mentioned penicillin derivatives, such as penicillin V, penicillin G, penicillin, ampicillin, amoxicillin, carbenicillin, ticarcillin, piperacillin, nafcillin, cloxacillin, dicloxacillin, monobactams such as aztreonam, and carbapenems such as imipenem.

In an embodiment of the invention the penicillin-type antibiotic composition comprising at least one modified release dosage form formulated so as to provide (or maintain) a concentration of the given penicillin-type antibiotic in the serum at or above the $MIC_{90}$ for an infecting bacterial pathogen for at least 5 hours within a 24-hour dosing interval, is further formulated so as to achieve Cmax in the serum for the total penicillin-type antibiotic released from the composition in less than about 12 hours following administration of the penicillin-type antibiotic composition, or following initial release of penicillin-type antibiotic from the penicillin-type antibiotic composition. In this embodiment (as in all embodiments) the dosage form(s) is/are further formulated such that the penicillin-type antibiotic composition provides (and preferably maintains) a serum concentration of the given penicillin-type antibiotic that is $\geq 0.06$ μg/mL., and such that the penicillin-type antibiotic composition contains the total dosage of the given penicillin-type antibiotic for a 24-hour dosing interval.

In another embodiment of the present invention there is provided a penicillin-type antibiotic pharmaceutical composition which is comprised of at least two, preferably at least three, penicillin-type antibiotic dosage forms (at least one of which is a modified release dosage form). Such dosage forms are formulated so that each of the dosage forms has a different release profile and so that the composition provides (and preferably maintains) a penicillin-type antibiotic concentration in the patient's serum that equals or exceeds the pathogen's drug-specific $MIC_{90}$ for at least five hours (preferably for at least five consecutive hours) within the 24-hour period following administration.

In another embodiment of the invention there are at least two, preferably at least three dosage forms (at least one of which is a modified release dosage form), each of which has a different release profile, the release profile of each of the dosage forms being such that the dosage forms each start release of the penicillin-type antibiotic contained therein at different times after administration of the penicillin-type antibiotic composition, and the composition provides (and preferably maintains) a penicillin-type antibiotic concentration in the patient's serum that equals or exceeds the pathogen's drug-specific $MIC_{90}$ for at least five hours (preferably for at least five consecutive hours) within the 24-hour period following administration.

Thus, in accordance with this embodiment of the present invention, there is provided a single or unitary antibiotic composition that has contained therein at least two, preferably at least three penicillin-type antibiotic dosage forms (at least one of which is a modified release dosage form), each of which has a different release profile, whereby the penicillin-type antibiotic contained in each of such dosage forms is released at different times, and the penicillin-type antibiotic composition provides a daily dosage of penicillin-type antibiotic, such as to provide (or maintain) a serum concentration of penicillin-type antibiotic in a patient or subject at or above a bacterial pathogen's drug-specific $MIC_{90}$ for at least five hours (preferably at for least five consecutive hours) within the 24-hour period following administration.

In accordance with another embodiment of the invention, the antibiotic composition may be comprised of at least four different dosage forms, each of which starts to release the penicillin-type antibiotic contained therein at different times after administration of the penicillin-type antibiotic composition, and the composition provides (or maintains) a penicillin-type antibiotic concentration in the patient's serum that equals or exceeds the pathogen's drug-specific $MIC_{90}$ for at least five hours (preferably for at least five consecutive hours) within the 24-hour period following administration.

The penicillin-type antibiotic composition generally does not include more than five dosage forms with different release times.

In accordance with another embodiment, the penicillin-type antibiotic composition has an overall release profile such that when administered the maximum serum concentration of the total antibiotic released from the composition is reached in less than twelve hours, preferably in less than eleven hours, and that maximum serum concentration is at least equivalent to the drug-specific $MIC_{90}$ of the bacterial pathogen.

In all embodiments of the invention as herein-above and herein-below described the penicillin-type antibiotic is formulated so as to provide (or maintain) a penicillin-type antibiotic concentration in the patient's serum that equals or exceeds the pathogen's drug-specific MIC, for at least five hours (preferably for at least five consecutive hours) within a 24-hour period when administered once-a-day.

In all embodiments of the invention the composition is designed and intended to provide a serum concentration of $\geq 0.06$ μg/mL. of penicillin-type antibiotic for at least 5 hours.

In preferred embodiments of the invention the composition is designed and intended to provide a serum concentration of $\geq 0.06$ μg/mL. of penicillin-type antibiotic for at least 5 consecutive hours.

In accordance with one embodiment of the invention, there are at least three dosage forms (at least one of which is a modified release dosage form). One of the at least three dosage forms is an immediate release dosage form whereby initiation of release of the penicillin-type antibiotic therefrom is not substantially delayed after administration of the penicillin-type antibiotic composition. The second and third of the at least three dosage forms are delayed release dosage forms (each of which may be a pH sensitive or a non-pH sensitive delayed dosage form, depending on the type of penicillin-type antibiotic composition), whereby the penicillin-type antibiotic released therefrom is delayed until after initiation of release of the penicillin-type antibiotic from the immediate release dosage form. More particularly, the penicillin-type antibiotic released from the second of the at least two dosage forms achieves a Cmax (maximum serum concentration in the serum) at a time after the penicillin-type antibiotic released from the first of the at least three dosage forms achieves a Cmax in the serum, and the penicillin-type antibiotic released from the third dosage form achieves a Cmax in the serum after the Cmax of penicillin-type antibiotic released from the second dosage form and the overall Cmax is at least equivalent to the drug-specific $MIC_{90}$ of the baterial pathogen.

In one embodiment, the second of the at least two dosage forms initiates release of the penicillin-type antibiotic contained therein at least one hour after the first dosage form, with the initiation of the release therefrom generally occurring no more than six hours after initiation of release of penicillin-type antibiotic from the first dosage form of the at least three dosage forms.

As hereinabove indicated, some embodiments of the penicillin-type antibiotic composition may contain three, four, or more different dosage forms (provided that at least one is a modified release dosage form).

In one three-dosage form embodiment, the penicillin-type antibiotic released from the third dosage form reaches a Cmax at a time later than the Cmax is achieved for the penicillin-type antibiotic released from each of the first and second dosage forms. In a preferred embodiment, release of penicillin-type antibiotic from the third dosage form is started after initiation of release of penicillin-type antibiotic from both the first dosage form and the second dosage form. In one embodiment, Cmax for penicillin-type antibiotic released from the third dosage form is achieved within eight hours.

In another three-dosage form embodiment the release of penicillin-type antibiotic from the second dosage form may be contemporaneous with initiation of release of penicillin-type antibiotic from the first dosage form.

In another three-dosage form embodiment the release of penicillin-type antibiotic from the third dosage form may be contemporaneous with initiation of release of penicillin-type antibiotic from the second dosage form.

In another embodiment, the penicillin-type antibiotic composition may contain four dosage forms (at least one of which is a modified release dosage form), with each of the four dosage forms having different release profiles, whereby the penicillin-type antibiotic released from each of the four different dosage forms achieves a Cmax at a different time.

As hereinabove indicated, in an embodiment, irrespective of whether the antibiotic contains at least two or at least three or at least four different dosage forms each with a different release profile, Cmax for all the penicillin-type antibiotic released from the penicillin-type antibiotic composition is achieved in less than twelve hours, and more generally is achieved in less than eleven hours and is at least equivalent to the drug-specific $MIC_{90}$ of the bacterial pathogen.

In a preferred embodiment, the penicillin-type antibiotic composition is a once a day composition, whereby after administration of the penicillin-type antibiotic composition, no further composition is administered during the day; i.e., the preferred regimen is that the composition is administered only once over a twenty-four hour period. Thus, in accordance with this preferred embodiment, there is a single administration of an penicillin-type antibiotic composition with the penicillin-type antibiotic being released in a manner such that overall penicillin-type antibiotic release is effected with different release profiles in a manner such that the overall Cmax for the penicillin-type antibiotic composition is reached in less than twelve hours and is at least equivalent to the drug-specific $MIC_{90}$ of the bacterial pathogen. The term single administration means that the total penicillin-type antibiotic administered over a twenty-four hour period is administered at the same time, which can be a single tablet or capsule or two or more thereof, provided that they are administered at essentially the same time.

In general, each of the dosage forms in the penicillin-type antibiotic compositions may have one or more penicillin-type antibiotics, and each of the dosage forms may have the same penicillin-type antibiotic or different penicillin-type antibiotics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic may occur. Such "leakage" is not "release" as used herein.

In one four-dosage form embodiment, the fourth dosage form may be a sustained release dosage form or a delayed release dosage form. If the fourth dosage form is a sustained release dosage form, even though Cmax of the fourth dosage form is reached after the Cmax of each of the other dosage forms is reached, penicillin-type antibiotic release from such fourth dosage form may be initiated prior to or after release from the second or third dosage form.

The penicillin-type antibiotic composition of the present invention, as hereinabove described, may be formulated for administration by a variety of routes of administration. For example, the penicillin-type antibiotic composition may be formulated in a way that is suitable for topical administration; administration in the eye or the ear; rectal or vaginal administration; as a nasal preparation; by inhalation; as an injectable; or for oral administration. In a preferred embodiment, the penicillin-type antibiotic composition is formulated in a manner such that it is suitable for oral administration.

For example, in formulating the penicillin-type antibiotic composition for topical administration, such as by application to the skin, the dosage forms, each of which contains a penicillin-type antibiotic, may be formulated for topical administration by including such dosage forms in an oil-in-water emulsion, or a water-in-oil emulsion. In such a formulation, an immediate release dosage form may be in the continuous phase, and a delayed release dosage form may be in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide a penicillin-type antibiotic composition in the form of a patch, which includes penicillin-type antibiotic dosage forms having different release profiles, as hereinabove described.

In addition, the penicillin-type antibiotic composition may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the penicillin-type antibiotic composition having at least one modified release dosage form (whether or not combined with additional dosage forms to provide a plurality of different release profiles) may be formulated for rectal or vaginal administration, as known in the art. This may take the form of a cream, an emulsion, a suppository, or other dissolvable dosage form similar to those used for topical administration.

In a preferred embodiment, the penicillin-type antibiotic composition is formulated in a manner suitable for oral administration. Thus, for example, for oral administration, each of the dosage forms may be used as a pellet or a particle, with a pellet or particle then being formed into a unitary pharmaceutical composition, for example, in a capsule, or embedded in a tablet, or suspended in a liquid for oral administration.

Alternatively, in formulating an oral delivery system, each of the dosage forms of the composition may be formulated as a tablet, with each of the tablets being put into a capsule to produce a unitary antibiotic composition. Thus, as a non-limiting example, a three dosage form antibiotic composition may include a first dosage form in the form of a tablet that is an immediate release tablet, and may also include two or more additional tablets, each of which provides for a delayed release or a sustained release of the penicillin-type antibiotic, as hereinabove described, to provide (and preferably maintain) a serum concentration of the penicillin-type antibiotic at least equivalent to the drug-specific $MIC_{90}$ of the bacterial pathogen for at least five (preferably for at least five consecutive hours) hours within a 24-hour dosing interval.

The formulation of a penicillin-type antibiotic composition including at least three dosage forms with different release profiles for different routes of administration is deemed to be within the skill of the art from the teachings herein. As known in the art, with respect to delayed release, the time of release can be controlled by a variety of mechanisms such as pH, coating thickness, choice of polymer, and combinations of the foregoing.

In formulating a penicillin-type antibiotic composition in accordance with one embodiment of the invention, an immediate release dosage form of the composition generally provides from about 20% to about 50% of the total dosage of penicillin-type antibiotic to be delivered by the composition, with such immediate release dosage form generally providing at least 25% of the total dosage of the penicillin-type antibiotic to be delivered by the composition. In many cases, an immediate release dosage form provides from about 20% to about 30% of the total dosage of penicillin-type antibiotic to be delivered by the composition; however, in some cases it may be desirable to have an immediate release dosage form provide for about 45% to about 50% of the total dosage of penicillin-type antibiotic to be delivered by the composition.

The remaining dosage forms deliver the remainder of the penicillin-type antibiotic. If more than one modified release dosage form is used each of the modified release dosage forms may provide about equal amounts of penicillin-type antibiotic; however, they may also be formulated so as to provide different amounts.

In accordance with the present invention, each of the dosage forms contains the same penicillin-type antibiotic; however, each of the dosage forms may contain more than one penicillin-type antibiotic.

In one embodiment, where the composition contains one immediate release component and two modified release components, the immediate release component provides from 20% to 35% (preferably 20% to 30%), by weight, of the total penicillin-type antibiotic; where there are three modified release components, the immediate release component provides from 15% to 30%, by weight, of the total penicillin-type antibiotic; and where there are four modified release components, the immediate release component provides from 10% to 25%, by weight, of the total penicillin-type antibiotic.

With respect to the modified release components, where there are two modified release components, the first modified release component (the one released earlier in time) provides from 30% to 60%, by weight, of the total penicillin-type antibiotic provided by the two modified release components with the second modified release component providing the remainder of the penicillin-type antibiotic.

Where there are three modified release components, the earliest released component provides 20% to 35% by weight of the total penicillin-type antibiotic provided by the three modified release components, the next in time modified release component provides from 20% to 40%, by weight, of the penicillin-type antibiotic provided by the three modified release components and the last in time providing the remainder of the penicillin-type antibiotic provided by the three modified release components.

When there are four modified release components, the earliest modified release component provides from 15% to 30%, by weight, the next in time modified release component provides from 15% to 30%, the next in time modified release component provides from 20% to 35%, by weight, and the last in time modified release component provides from 20% to 35%, by weight, in each case of the total penicillin-type antibiotic provided by the four modified release components.

The Immediate Release Component

The immediate release portion of this system can be a mixture of ingredients that breaks down quickly after administration to release the penicillin-type antibiotic. This can take the form of either a discrete pellet or granule that is mixed in with, or compressed with, the other three components.

The materials to be added to the penicillin-type antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the range of 0.05-15% (W/W).

The non-pH Sensitive Delayed Release Component

The components in this composition are the same as the immediate release unit, but with additional polymers integrated into the composition, or as coatings over the pellet or granule.

Several methods to affect a delayed release with non-pH dependent polymers are known to those skilled in the art. These include soluble or erodible barrier systems, enzymatically degraded barrier systems, rupturable coating systems, and plugged capsule systems among others. These systems have been thoroughly described in the literature (see "A Review of Pulsatile Drug Delivery" by Bussemer and Bodmeier in the Winter 2001 issue of American Pharmaceutical Review) and formulations and methods for their manufacture are hereby incorporated by reference.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5-25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose; hydroxypropylmethylcellulose; hydroxypropylcellulose; hydroxyethylcellulose; carboxymethylcellulose; methylcellulose; nitrocellulose; Eudragit R; Eudragit RS; and Eudragit RL; Carbopol; or polyethylene glycols with molecular weights in excess of 8,000 daltons.

These materials can be present in concentrations from 4-20% (W/W).

When it is desired to delay inititiation of release of the sustained release dosage form, an appropriate coating may be used to delay inititiation of the sustained release, such as a pH sensitive or a non-pH sensitive coating.

The non-pH Sensitive Coating for Sustained Release Dosage Form

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit RS), cellulose acetate, and ethylcellulose.

Typically these materials can be present in the range of 0.5-25% (W/W) of this component. Preferably the materials are present in an amount just enough to provide the desired in vivo lag time and $T_{max}$.

The pH Sensitive Coating for Sustained Release Dosage Form

The kind of materials useful for this purpose can be, but are not limited to, cellulose acetate pthalate, Eudragit L, Eudragit S, Eudragit FS, and other pthalate salts of cellulose derivatives.

These materials can be present in concentrations from 4-20% (W/W) or more. Preferably the materials are present in an amount just enough to provide the desired in vivo lag time and $T_{max}$.

As hereinabove indicated, the units comprising the penicillin-type antibiotic composition of the present invention can be in the form of discrete pellets or particles contained in the capsule, or particles embedded in a tablet or suspended in a liquid suspension.

The penicillin-type antibiotic composition of the present invention may be administered, for example, by any of the following routes of administration: sublingual, transmucosal, transdermal, parenteral, etc., and preferably is administered orally. The composition includes a therapeutically effective amount of the penicillin-type antibiotic, which amount will vary with the penicillin-type antibiotic to be used, the disease or infection to be treated, and the number of times that the composition is to be delivered in a day. The composition is administered to a patient or subject in an amount effective for treating a bacterial infection.

This system will be especially useful in extending the practical therapeutic activity for antibiotics with elimination half lives of less than 20 hours and more particularly with elimination half-lives of less than 12 hours, and will be particularly useful for those drugs with half-lives of 2-10 hours. The following are examples of some antibiotics with half-lives of about 1 to 12 hours: imipenem, ertapenem, (carbapenems) penicillin V, penicillin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) mezlocillin, piperacillin, piperacillin and taxobactam, ticarcillin, ticarcillin and clavulanate potassium, (penicillins).

The penicillin-type antibiotic composition should be administered for a sufficient amount of time to treat the infection. In one embodiment the penicillin-type antibiotic composition is administered for 10 days.

The invention will be further described with respect to the following examples; however, the scope of the invention is not limited thereby. All percentages in this specification, unless otherwise specified, are by weight.

The following examples detail the general procedures for making immediate release, delayed release (both pH sensitive and non-pH sensitive types), sustained release, and delayed sustained release components for the dosage form of the present invention. Any combination of the components that results in the desired time above MIC would be included as part of this disclosure. Specific examples of combinations of the components are given, but are not limited to the ones described herein. Additionally, there is an example of a multi-unit dosage form specific to amoxicillin type tablets, but any appropriate therapeutic agent could be substituted.

EXAMPLES

I. Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum oven or forced-air oven. The product may be sieved or granulated, and compressed using a suitable tablet press, such as a rotary tablet press, or filled into a capsule or sachet with a suitable filler.

|  | Ingredient | Conc. (% W/W) |
| --- | --- | --- |
| Example 1: | Amoxicillin | 65% (W/W) |
|  | Microcrystalline cellulose | 20 |
|  | Povidone | 10 |
|  | Croscarmellose sodium | 5 |
| Example 2: | Amoxicillin | 55% (W/W) |
|  | Microcrystalline cellulose | 25 |
|  | Povidone | 10 |
|  | Croscarmellose sodium | 10 |
| Example 3: | Amoxicillin | 65% (W/W) |
|  | Microcrystalline cellulose | 20 |
|  | Hydroxypropylcellulose | 10 |
|  | Croscarmellose sodium | 5 |
| Example 4: | Amoxicillin | 75% (W/W) |
|  | Polyethylene glycol 4000 | 10 |
|  | Polyethylene glycol 2000 | 10 |
|  | Hydroxypropylcellulose | 5 |
| Example 5: | Amoxicillin | 75% (W/W) |
|  | Polyethylene glycol 8000 | 20 |
|  | Polyvinylpyrrolidone | 5 |
| Example 6: | Clarithromycin | 65% (W/W) |
|  | Microcrystalline cellulose | 20 |
|  | Hydroxypropylcellulose | 10 |
|  | Croscarmellose sodium | 5 |
| Example 7: | Clarithromycin | 75% (W/W) |
|  | Microcrystalline cellulose | 15 |
|  | Hydroxypropylcellulose | 5 |
|  | Croscarmellose sodium | 5 |
| Example 8: | Clarithromycin | 75% (W/W) |
|  | Polyethylene glycol 4000 | 10 |
|  | Polyethylene glycol 2000 | 10 |
|  | Hydroxypropylcellulose | 5 |
| Example 9: | Clarithromycin | 75% (W/W) |
|  | Polyethylene glycol 8000 | 20 |
|  | Polyvinylpyrrolidone | 5 |
| Example 10: | Ciprofloxacin | 65% (W/W) |
|  | Microcrystalline cellulose | 20 |
|  | Hydroxypropylcellulose | 10 |
|  | Croscarmellose sodium | 5 |
| Example 11: | Ciprofloxacin | 75% (W/W) |
|  | Microcrystalline cellulose | 15 |
|  | Hydroxypropylcellulose | 5 |
|  | Croscarmellose sodium | 5 |
| Example 12: | Ciprofloxacin | 75% (W/W) |
|  | Polyethylene glycol 4000 | 10 |
|  | Polytheylene glycol 2000 | 10 |
|  | Hydroxypropylcellulose | 5 |
| Example 13: | Cirpofloxacin | 75% (W/W) |
|  | Polyethylene glycol 8000 | 20 |
|  | Polyvinylpyrrolidone | 5 |
| Example 14: | Ceftibuten | 75% (W/W) |
|  | Polyethylene glycol 4000 | 10 |
|  | Polyethylene glycol 2000 | 10 |
|  | Hydroxypropylcellulose | 5 |
| Example 15: | Ceftibuten | 75% (W/W) |
|  | Polyethylene Glycol 4000 | 20 |
|  | Polyvinylpyrrolidone | 5 |

II. non-pH Sensitive Delayed Release Component

Any of the methods described in "A Review of Pulsatile Drug Delivery" by Bussemer and Bodmeier in the Winter 2001 issue of American Pharmaceutical Review may be utilized to make the pH independent delayed release component described. Examples 16 and 17 utilize an organic acid layer underneath a layer of Eudragit RS to result in a rapid increase in the permeability of the Eudragit film after a set amount of time depending on the permeability and thickness of the film thus allowing the inner core to release through the Eudragit membrane. Example 18 utilizes a core with a highly swellable polymer that ruptures the insoluble coating membrane after a certain amount of time determined by the permeability, plasticity and thickness of the external cellulose acetate membrane. The coatings are applied to the core via methods such as wurster column coating in a fluid bed processor as known to those skilled in the art.

Additionally, this component may be formed as in example 19. In this example the component is prepared by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven.

After the component is allowed to cool, the product may be sieved or granulated, and compressed using a suitable tablet press, such as a rotary tablet press, or filled into a capsule with a suitable encapsulator.

|  | Ingredient | Conc. (% W/W) |
|---|---|---|
| Example 16: | Core from Example 4 | 65% (W/W) |
|  | Citric Acid | 10 |
|  | Eudragit RS Polymer | 20 |
|  | Talc | 4 |
|  | TEC | 1 |
| Example 17: | Core from Example 9 | 75% (W/W) |
|  | Citric Acid | 10 |
|  | Eudragit RS Polymer | 10 |
|  | Talc | 4 |
|  | TEC | 1 |
| Example 18: | Core from Example 1 | 93% (W/W) |
|  | Cellulose Acetate | 6.75 |
|  | PEG 400 | 0.25 |
| Example 19: | Ciprofloxacin | 70% (W/W) |
|  | Polyox | 20 |
|  | Hydroxypropylcellulose | 5 |
|  | Croscarmellose sodium | 5 |

III. Enteric Release Component

Examples 20-27 utilize film coating techniques commonly known to those skilled in the art to create the enteric release component by layering of such enteric polymers onto an active core. In general the steps involve first making a coating dispersion or solution in organic or aqueous solvent. Second, the coating is applied at the proper conditions to produce an acceptably uniform film. This is done in a suitable coating apparatus such as a pan coater or a fluid bed wurster column coater. Optionally the product may be further cured if necessary.

To create a matrix type enteric component, formulate the ingredients of examples 28-32 by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool.

The product produced by either manner may be sieved or granulated, and compressed using a suitable tablet press, such as a rotary tablet press, or filled into capsules using a suitable capsule filler such as a MG2 Futura.

|  | Ingredient | Conc. (% W/W) |
|---|---|---|
| Example 20: | Core from Example 1 | 65% (W/W) |
|  | Cellulose Acetate Pthalate | 30 |
|  | TEC | 5 |
| Example 21: | Core from Example 5 | 75% (W/W) |
|  | Cellulose Acetate Pthalate | 20 |
|  | Triacetin | 5 |
| Example 22: | Core from Example 1 | 65% (W/W) |
|  | Eudragil L | 25 |
|  | Talc | 8 |
|  | TEC | 2 |
| Example 23: | Core from Example 1 | 65% (W/W) |
|  | Eudragit FS | 28 |
|  | Talc | 5 |
|  | TEC | 2 |
| Example 24: | Core from Example 1 | 65% (W/W) |
|  | Eudragit S | 28 |
|  | Talc | 5 |
|  | TEC | 2 |
| Example 25: | Core from Example 7 | 75% (W/W) |
|  | Eudragit L | 20 |
|  | Talc | 3.5 |
|  | TEC | 1.5 |
| Example 26: | Core from Example 11 | 60% (W/W) |
|  | Eudragit L | 35 |
|  | Talc | 4 |
|  | TEC | 1 |
| Example 27: | Core from Example 15 | 65% (W/W) |
|  | Cellulose Acetate Pthalate | 32.5 |
|  | TEC | 2.5 |
| Example 28: | Amoxicillin | 75% (W/W) |
|  | Microcrystalline Cellulose | 5 |
|  | Hydroxypropylcellulose pthalate | 20 |
| Example 29: | Amoxicillin | 60% (W/W) |
|  | Lactose | 10 |
|  | Eudragit L 30D | 30 |
| Example 30: | Ciprofloxacin | 70% (W/W) |
|  | Polyethylene glycol 4000 | 10 |
|  | Cellulose acetate pthalate | 20 |
| Example 31: | Clarithromycin | 60% (W/W) |
|  | Polyethylene glycol 2000 | 10 |
|  | Lactose | 20 |
|  | Eudragit L 30D | 10 |
| Example 32: | Ceftibuten | 70% (W/W) |
|  | Microcrystalline cellulose | 20 |
|  | Cellulose acetate pthalate | 10 |

IV. Sustained Release Component

Examples 33-38 utilize film coating techniques commonly known to those skilled in the art to create the sustained release component by layering of such sustained release polymers onto an active core. In general the steps involve first making a coating dispersion or solution in organic or aqueous solvent. Second, the coating is applied at the proper conditions to produce an acceptably uniform film. This is done in a suitable coating apparatus such as a pan coater or a fluid bed wurster column coater. Optionally the product may be further cured if necessary. Curing studies are recommended with sustained release membranes.

To create a matrix type sustained release component, formulate the ingredients of example 39-42 by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum oven or forced-air oven. Allow the product to cool.

The product produced by either manner may be sieved or granulated, and compressed using a suitable tablet press, such as a rotary tablet press, or filled into capsules using a suitable capsule filler such as a MG2 Futura.

|  | Ingredient | Conc. (% W/W) |
|---|---|---|
| Example 33: | Core from Example 1 | 75% (W/W) |
|  | Ethylcellulose | 20 |
|  | HPC | 5 |
| Example 34: | Core from Example 5 | 80% (W/W) |
|  | Eudragit RS | 10 |
|  | Eudragit RL | 5 |
|  | Talc | 3 |
|  | TEC | 2 |

-continued

|  | Ingredient | Conc. (% W/W) |
|---|---|---|
| Example 35: | Core from Example 5 | 90% (W/W) |
|  | Ethylcellulose | 9 |
|  | Triacetin | 1 |
| Example 36: | Core from Example 7 | 90% (W/W) |
|  | Surelease | 10 |
| Example 37: | Core from Example 11 | 85% (W/W) |
|  | Kollicoat SR | 10 |
|  | TBC | 5 |
| Example 38: | Core from Example 15 | 80% (W/W) |
|  | Polyethylene glycol 8000 | 5 |
|  | Eudgragit RS 30D | 15 |
| Example 39: | Amoxicillin | 75% (W/W) |
|  | Hydroxyethylcellulose | 10 |
|  | Polyethylene glycol 4000 | 10 |
|  | Hydroxypropylcellulose | 5 |
| Example 40: | Ciprofloxacin | 75% (W/W) |
|  | Lactose | 10 |
|  | Povidone (PVP) | 10 |
|  | Polyethylene glycol 2000 | 5 |
| Example 41: | Clarithromycin | 75% (W/W) |
|  | Polyethylene glycol 4000 | 10 |
|  | Povidone (PVP) | 10 |
|  | Hydroxypropylcellulose | 5 |
| Example 42: | Ceftibuten | 75% (W/W) |
|  | Lactose | 15 |
|  | Polyethylene glycol 4000 | 5 |
|  | Polyvinylpyrrolidone | 5 |

III. Sustained Release Dosage Form with Coating to Delay Initiation of Sustained Release:

Delaying the initiation of the sustained release of antibiotic in the present invention is achieved by either coating the immediate release component bead with a sustained release coating and then subsequently applying an enteric coating or non pH sensitive delayed release coating to that coated bead, or alternatively the sustained release matrix component bead may be coated with an enteric coating or non pH sensitive delayed release coating.

Coatings can be applied to either the sustained release coated beads or the sustained release matrix beads to form a product which pulses the therapeutical agent in a desired environment or location of the GI tract.

III A. The following examples describe the detailed preparation of the sustained-release coating materials to be applied to the immediate release beads from section I of the examples, resulting in a sustained release component of the invention.

Example 43

Eudragit RS Example—Organic Coating

| Component Part A | Percentage (%) |
|---|---|
| Eudragit RS-100 | 6.0 |
| Triethyl Citrate | 1.0 |
| Talc | 0.5 |
| Acetone | 92.5 |

Step 1. Dissolve Eudragit in Acetone.
Step 2. Mix TEC and talc in a separate container with some Acetone.
Step 3. Add step 2 to Step 1, and allow to mix for 20 minutes before spraying.

Example 44

Surelease™ Example—Aqueous Coating

| Component Part A | Percentage (%) |
|---|---|
| Surelease | 90 |
| Purified Water | 10.0 |

Step 1. Mix surelease and water for 30 minutes before spraying.

Directions for application of the sustained release coating to the beads:

Charge a wurster column equipped fluid bed with the beads to be coated. Spray the coating onto the beads at a rate and temperature known to those skilled in the art of bead coating so as to efficiently coat the beads to give a weight gain of between 4 and 20%. Dry the beads to the specified level of coating solvent for optimum handling and stability. Cure the beads for additional congealing of the sustained release film if required.

III B. The following are examples of the pH sensitive, or enteric release, coating that can be used to optionally delay the onset of action of any or all of the second, third, or additional dosage forms.

The composition of the aqueous Eudragit L30D-55 dispersion to be applied to the immediate release components that have been treated with the above-described sustained release coatings, or to the sustained-matrix pellets is provided below in Example 45.

Example 45

Eudragit® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

Preparation Procedure for an Eudragit® L 30 D-55 Aqueous Dispersion

Step 1 Suspend triethyl citrate and talc in deionized water.
Step 2 The TEC/talc suspension is then homogenized using a PowerGen 700 high shear mixer.
Step 3 Add the TEC/talc suspension slowly to the Eudragit® L 30 D-55 latex dispersion while stirring.
Step 4 Allow the coating dispersion to stir for one hour prior to application onto the matrix pellets.

Example 46

Preparation of an Eudragit® S 100 Aqueous Coating Dispersion

Dispersion Formulation

The composition of the aqueous Eudragit® S 100 dispersion applied to the matrix pellets is provided below:

| Eudragit ® S 100 Aqueous Coating Dispersion | |
|---|---|
| Component | Percentage (%) |
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

Preparation Procedure for an Eudragit® S 100 Aqueous Dispersion

Part I:
(i) Dispense Eudragit® S 100 powder in deionized water with stirring.
(ii) Add ammonium hydroxide solution drop-wise into the dispersion with stirring.
(iii) Allow the partially neutralized dispersion to stir for 60 minutes.
(iv) Add triethyl citrate drop-wise into the dispersion with stirring. Stir for about 2 hours prior to the addition of Part B.

Part II:
(i) Disperse talc in the required amount of water
(ii) Homogenize the dispersion using a PowerGen 700D high shear mixer.
(iii) Part B is then added slowly to the polymer dispersion in Part A with a mild stirring.

Coating Conditions for the Application of Aqueous Coating Dispersions

The following coating parameters were used to coat matrix pellets with each of the Eudragit® L 30 D-55 and Eudragit® S 100 aqueous film coating.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
(ii) Coat matrix pellets with S100 dispersion such that you apply 20% coat weight gain to the pellets.

III. C. The following examples describe the detailed preparation of the non pH sensitive coating materials to be used to optionally delay the onset of action of any or all of the second, third, or additional dosage forms.

Example 47

Rupturable Film

| Component Part A | Percentage (%) |
|---|---|
| Cellulose Acetate 398-10 | 6.0 |
| PEG 400 | 1.5 |
| Acetone | 92.5 |

Step 1. Dissolve cellulose acetate in Acetone.
Step 2. Add TEC to Step 1, and allow to mix for 20 minutes.

Directions for application of the sustained release coating to the beads:

Charge a wurster column equipped fluid bed with the beads to be coated. The beads must contain a component which will swell rapidly upon exposure to moisture. Beads containing croscarmellose sodium in Section I are good candidates as are beads with swellable hydrophilic polymers from Section II. Spray the coating onto the beads at a rate and temperature known to those skilled in the art of bead coating so as to efficiently coat the beads to give a weight gain of between 4 and 20%. Dry the beads to the specified level of coating solvent for optimum handling and stability.

Coating Conditions for the Application of the Rupturable Film Coating.

The following coating parameters were used to coat matrix mini tablets from a previous example with the rupturable film coating. A 2.5% weight gain provided the desired lag time.

| Coating Equipment | Vector LDCS Coating System with 1.3 L pan |
|---|---|
| Spray nozzle diameter | 0.8 mm |
| Material Charge | 800 grams |
| Inlet Air Temperature | 40 to 45° C. |
| Outlet Air Temperature | 18 to 23° C. |
| Atomization Air Pressure | 25 psi |
| Pump Rate | 6 grams per minute |

The enteric coatings and non-pH sensitive coatings as described above can be applied to either a sustained release matrix bead as in examples 16-25, or to the immediate release component beads that have been previously treated with a sustained release coating, to thereby provide a sustained release bead with a delayed onset of action. In addition, the enteric coating or non-pH sensitive coating can be applied to the immediate release component bead directly to provide delayed onset of action.

IV. Example Final Compositions

After one or all of the desired individual components are manufactured, the final dosage form is assembled and may take the shape of a tablet, capsule or sachet. Preferably the final dosage form takes the shape of a capsule or tablet. Most preferably the final dosage form is a tablet.

One or more of the individual components can be used to achieve the desired T>MIC. If one were to include three components in one's dosage form then preferably the first, second, and third dosage forms provide 20-70%, 10-70% and 10-70% of the total dosage form, respectively. More preferably the ratio of first, second and third dosage forms are in the range of 25-66%, 15-60% and 15-60% of the total dosage form respectively. Most preferably the ratio of the first, second and third dosage forms are in the range of 33-60%, 25-50%, and 25-50% respectively. One can also utilize one, two, three, or four or more components, and balance the ratio of the components in such a way to meet the T>MIC criteria.

V. Example of Three Component Amoxicillin Tablet and Sprinkle Dosage Forms

V-1. Description of the Dosage Form

API content can range for example from 10 to 80% therapeutic compound, and in the case the therapeutic compound is amoxicillin, it most preferably would contain 775 mg amoxicillin. The tablet can be of any desired shape, with a target gross weight of approximately 1500 mg. The tablet can optionally be coated with a film, and/or imprinted.

The following specific example is written for components that contain amoxicillin, however other therapeutic agents can be substituted with proper proportion adjustments known to one skilled in the art of oral dosage form development.

The tablet of this invention is a rapidly disintegrating formulation containing three active intermediate compositions, an immediate-release granulation (Amoxicillin Granules) and two functionally coated delayed-release pellets (Amoxicillin Pulse 2 Pellets and Amoxicillin Pulse 3 Pellets). Non-functional, color and clear film coats are optionally applied to the outer surface and/or the coated tablets are imprinted.

FIG. 1 is a flowchart describing the General Procedure to Make a Multiparticulate Tablet.

Table 1 provides the qualitative and quantitative composition of three example amoxicillin tablet formulations on a weight to weight (w/w %) basis of individual ingredients. For formulation B, an example set of procedures and component compositions for making this type of tablet is expanded. Table 2 provides the qualitative and quantitative composition of an example amoxicillin Tablet formulation on the basis of the tablet core, coatings, and its active intermediate compositions. Tables 3, 4, 5, and 6 provide the qualitative and quantitative composition of the Amoxicillin Granules, Amoxicillin Core Pellets, Amoxicillin Pulse 2 Pellets, and Amoxicillin Pulse 3 Pellets, respectively. An optional coating can be applied and optional tablet imprinting can be used to complete the product presentation.

TABLE 1

Example Quantitative Compositions of Example Amoxicillin Tablets.

| Component | A (w/w %) | B (w/w %) | C (w/w %) |
|---|---|---|---|
| Amoxicillin, USP | 78.476 | 59.524 | 62.821 |
| Silicified Microcrystalline Cellulose | 0.000 | 20.676 | 21.900 |
| Crospovidone, NF | 0.000 | 3.892 | 4.100 |
| Methacrylic Acid Copolymer Dispersion, NF | 4.272 | 2.926 | 2.879 |
| Opadry ® Blue[1] | 0.000 | 2.415 | 0.000 |
| Talc, USP | 3.617 | 2.036 | 1.804 |
| Hydroxypropyl Methylcellulose Acetate Succinate[1] | 4.107 | 1.939 | 1.229 |
| Microcrystalline Cellulose, NF | 4.276 | 1.787 | 1.545 |
| Povidone, USP | 1.716 | 1.546 | 1.691 |
| Opadry ® Clear[1] | 0.000 | 0.966 | 0.000 |
| Magnesium Stearate, NF | 0.000 | 0.966 | 1.000 |
| Triethyl Citrate, NF | 1.806 | 0.939 | 0.694 |
| Polyoxyl 35 Castor Oil, NF | 0.843 | 0.345 | 0.299 |
| Sodium Lauryl Sulfate, NF | 0.129 | 0.062 | 0.039 |

TABLE 1-continued

Example Quantitative Compositions of Example Amoxicillin Tablets.

| Component | A (w/w %) | B (w/w %) | C (w/w %) |
|---|---|---|---|
| Opadry II White, 33G28523 | 0.761 | 0.000 | 0.000 |
| Opacode ® Black[1] | 0.000 | Trace Amount | 0.0 |
| Purified Water, USP[1] | * | * | * |
| Total | 100.0 | 100.0 | 100.0 |

[1]Water removed during processing

TABLE 2

Composition of an Example Amoxicillin Tablet by component.

| Core Tablet | w/w % |
|---|---|
| Amoxicillin Granules | 28.6 |
| Amoxicillin Pulse 2 Pellets | 24.1 |
| Amoxicillin Pulse 3 Pellets | 20.9 |
| Silicified Microcrystalline Cellulose | 21.4 |
| Crospovidone | 4.0 |
| Magnesium Stearate | 1.0 |
| Core Tablet Weight | 100 |

V-2 Amoxicillin Granules

TABLE 3

Qualitative and Quantitative Composition of Amoxicillin Granules

| Component | w/w % |
|---|---|
| Amoxicillin | 97.0 |
| Povidone | 3.0 |
| Purified Water[1] | N/A |
| Total Amoxicillin Granules | 100 |

[1]Water removed during processing

General Procedure for Manufacturing Amoxicillin Granules:

A standard wet granulation process known to one skilled in the art is used for preparation of the Amoxicillin Granules. The wet granules are discharged and fed into a Dome Extrusion Granulator. The wet extruded granules are then dried for a fixed period of time or until the LOD (loss on drying) of the granules is suitable for the formulation, typically less than 15%. The dried granules are then sized in a Rotating Impeller Screening Mill. The milled material is collected into drums.

V-3 Amoxicillin Core Pellets

The Core Pellets are used as the starting material for the later preparation of the Pulse 2 Pellets and the Pulse 3 Pellets used in the tablet preparation. They also serve as the core pellet for the immediate release pellet in the sprinkle dosage form. The core pellets are prepared using the unit operations of wet granulating, extruding, spheronizing, fluid bed drying and sizing. The composition of the core pellets is listed in Table 4.

TABLE 4

Composition of Amoxicillin Core Pellets

| Amoxicillin Trihydrate (92%) Pellet Component | w/w % |
|---|---|
| Amoxicillin Trihydrate, Powder Grade, USP | 92.0 |
| Microcrystalline Cellulose, NF | 5.0 |

TABLE 4-continued

Composition of Amoxicillin Core Pellets

| Amoxicillin Trihydrate (92%) Pellet Component | w/w % |
|---|---|
| Povidone K30, USP | 2.0 |
| Polyoxyl 35 Castor Oil, NF | 1.0 |
| Total | 100 |

V-4 Amoxicillin Pulse 2 Pellets

Table 5 lists the composition of the example Amoxicillin Pulse 2 Pellets.

TABLE 5

Composition of Amoxicillin Pulse 2 Pellets

| Component | w/w % |
|---|---|
| Amoxicillin | 76.6 |
| Microcrystalline Cellulose (Avicel ® PH-101) | 4.19 |
| Povidone (Kollidon 30) | 1.69 |
| Polyoxyl 35 Castor Oil (Cremophor EL) | 0.80 |
| Methacrylic Acid Copolymer Dispersion (Eudragit ® L30D-55)[1] | 10.41 |
| Talc | 5.19 |
| Triethyl Citrate | 1.00 |
| Purified Water[2] | N/A |
| Total Amoxicillin Pulse 2 Pellets | 100.0 |

[1]Amount per tablet of the solids content
[2]Water removed during processing

The Amoxicillin Pulse 2 Pellets are prepared by coating the previously prepared Amoxicillin Core Pellets with a functional film coat of methacrylic acid copolymer dispersion, 20% w/w. Prior to the coating process, a dispersion of the methacrylic acid copolymer is made according to the manufacturer's instructions. The dispersion is applied to the Amoxicillin Core pellets using a Fluid Bed Bottom Spray Coater, equipped with appropriate spray nozzles and a fixed column gap distance.

The pellets are then appropriately sized. The Amoxicillin Pulse 2 Pellets may be held in ambient warehouse conditions until further processing.

V-5 Amoxicillin Pulse 3 Pellets

The amoxicillin pulse 3 pellets are prepared by coating the previously prepared Amoxicillin Core Pellets with a 5% w/w subcoat of methacrylic acid copolymer, followed by a 20% w/w functional film coat of hypromellose acetate succinate.

Table 6 lists the composition of the example amoxicillin Pulse 3 pellets

TABLE 6

Composition of Amoxicillin Pulse 3 Pellets

| Component | Amount/Tablet (mg) |
|---|---|
| Amoxicillin | 222.6 |
| Microcrystalline Cellulose (Avicel ® PH-101) | 12.1 |
| Povidone (Kollidon 30) | 4.8 |
| Polyoxyl 35 Castor Oil (Cremophor EL) | 2.4 |
| Methacrylic Acid Copolymer Dispersion (Eudragit ® L30D-55)[1] | 7.6 |
| Hypromellose Acetate Succinate (AQOAT AS-HF) | 29.0 |
| Talc | 12.4 |
| Triethyl Citrate | 10.6 |

TABLE 6-continued

Composition of Amoxicillin Pulse 3 Pellets

| Component | Amount/Tablet (mg) |
|---|---|
| Sodium Lauryl Sulfate | 0.9 |
| Purified Water[2] | N/A |
| Total Amoxicillin Pulse 3 Pellets | 302.4 |

[1]Amount per tablet of the solids content
[2]Water removed during processing

Prior to the subcoating process, a dispersion of the methacrylic acid copolymer is made according to the manufacturer's instructions. The second coating material, the hypromellose acetate succinate dispersion is prepared according to the manufacturer's instructions. The subcoat layer, is then applied to the Amoxicillin Core Pellets using the same Fluid Bed Bottom Spray Coater as used for preparation of the Pulse 2 Pellets.

The hypromellose acetate succinate coating dispersion is then immediately applied to the sub-coated pellets still in the Fluid Bed Bottom Spray Coater. The atomization air used for the second coating process is set at the same pressure as used for the sub coating process. The coating process is complete when all of the dispersion has been applied. Following a drying period the final coated pellets are cooled.

The coated, dried and cooled Amoxicillin Pulse 3 Pellets are collected into lined drums The coated Pulse 3 Pellets are then sized. The Amoxicillin Pulse 3 Pellets may be held in ambient warehouse conditions until further processing.

V-6 Tabletting 1.2 The amoxicillin granules, pulse 2 pellets and pulse 3 pellets can be combined at the desired ratio and compressed on a rotary or other type of tablet press with suitable tooling installed for the desired size tablet. Ratios of Pulses or pellets can vary depending on the absorption characteristics of the desired drug. Ratios can range from front loaded (middle loaded or back loaded as per discussion in the specs section. The percent of each component can range from 10-90% for each of the at least 3 components in this example. For example, but not in anyway limiting, pulse 1 can be 10%, pulse 2 can be 80% and pulse 3 can be 10%. Or, as an alternate non-limiting example, pulse 1 can be 30%, pulse 2 can be 50% and pulse 3 can be 20%. In a preferred embodiment the tablet is manufactured by combining the immediate-release granulation (Pulse 1, 45%) with two functionally coated delayed-release pellets (Pulse 2, 30% and Pulse 3, 25%).

V-7 Optional Coatings

An additional optional coating can be applied to the tablet, or directly to the core, pulse 2 and pulse 3 pellets according to the manufacturer's recommendation for the coating process conditions and procedures.

An optional printing on the tablets can be done using a formula as supplied by the manufacturer or as modified to suit the tablet characteristics. Additional optional ingredients are Microcrystalline Cellulose and Colloidal Silicon Dioxide. These can be added to prevent tacking and sticking if necessary. These two materials can be optionally obtained as the composition Prosolv SMCC® 90 (FMC).

V-8 Sprinkle Dosage Form

These coated or uncoated pellets can be filled to give the desired dose into an appropriate dosing device at the desired ratios as described above either separately or all together, such as a sachet, capsule, or other means of delivering the material to the consumer.

For example the core pellets may be coated with a non-functional immediate release film coating to produce Pulse 1 pellets. The Pulse 1 pellets as well as Pulse 2 and Pulse 3 pellets may be used as a sprinkle product by placing the Pulse 1, Pulse 2 and Pulse 3 pellets in a sachet, capsule or other form that can be used for simultaneous delivery of the three pulses in a particulate form. In one embodiment, Pulse 1, Pulse 2 and Pulse 3 are combined to provide 45%, 30% and 25% of Pulse 1, Pulse 2, and Pulse 3, respectively.

Such combination of Pulses 1, 2 and 3 may be formulated into a sprinkle product; e.g., a twice-a-day product that contains 475 mg or 775 mg of amoxicillin. In another embodiment, Pulse 1, 2 and 3 may be combined into a once-a-day sprinkle product that contains 775 mg or 1250 mg or 1550 mg of amoxicillin. The sprinkle product may be sprinkled over applesauce, yogurt, or other soft food for administration. The product should not be chewed or crushed.

Numerous modification and variations of the present invention are possible in light of the above teachings and therefore within the scope of the appended claims the invention may be practiced otherwise than as particularly described. The present invention also extends to formulations which are bioequivalent to the pharmaceutical formulations of the present invention, in terms of both rate and extent of absorption, for instance as defined by the US Food and Drug Administration and discussed in the so-called "Orange Book" (Approved Drug Compositions with Therapeutic Equivalence Evaluations, US Dept of Health and Human Services, 19th edn, 1999).

What is claimed is:

1. A once-a-day amoxicillin antibiotic product comprising; first, second, and third amoxicillin antibiotic dosage forms, each of said amoxicillin antibiotic dosage forms comprising at least one amoxicillin antibiotic and a pharmaceutically acceptable carrier, said first amoxicillin antibiotic dosage form being, an immediate release dosage form, said second and third amoxicillin antibiotic dosage forms being delayed release: dosage forms, wherein said second amoxicillin antibiotic dosage form comprises amoxicillin coated with a methacrylic acid copolymer dispersion and said third amoxicillin antibiotic dosage form comprises amoxicillin coated with a first layer of a methacrylic acid copolymer dispersion and a second layer of hypromellose acetate succinate, and wherein each of said first, second, and third amoxicillin antibiotic dosage forms initiates release at different times, Cmax of the total amoxicillin antibiotic released from said amoxicillin antibiotic product is achieved in less that about 12 hours from administration; wherein said product contains the total dosage of amoxicillin, for a 24-hour dosing interval.

2. The product of claim 1, wherein said total dosage of amoxicillin is from about 775 mg to about 1550 mg.

3. The product of claim 1, wherein said first amoxicillin antibiotic dosage form comprises 10-90% of the product, wherein said second amoxicillin antibiotic dosage form comprises 10-90% of the product, and wherein said third amoxicillin antibiotic dosage form comprises 10-90% of the product.

4. The product of claim 3, wherein said first amoxicillin antibiotic dosage form comprises 45% of the product, wherein said, second amoxicillin antibiotic dosage form comprises 30% of the, product, and wherein said third amoxicillin antibiotic dosage form comprises 25% of the product.

5. The product of claim 1, wherein when the product is administered to a patient or subject in need thereof, the product provides a concentration of amoxicillin in the serum at or above the $MIC_{90}$ for an infecting bacterial pathogen for at least 5 hours within a 24-hour dosing interval.

6. The product of claim 1, wherein said second and third amoxicillin antibiotic dosage forms further comprise microcrystalline cellulose, povidone, and polyoxyl 35 castor oil.

7. The product of claim 1, wherein amoxicillin is the only antibiotic present in the first, second, and third amoxicillin antibiotic dosage forms.

* * * * *

UNITED STATES PATENT AND TRADEMARK OFFICE
CERTIFICATE OF CORRECTION

PATENT NO.         : 8,357,394 B2                                          Page 1 of 1
APPLICATION NO.    : 11/636291
DATED              : January 22, 2013
INVENTOR(S)        : Henry H. Flanner et al.

It is certified that error appears in the above-identified patent and that said Letters Patent is hereby corrected as shown below:

In the Claims

Col. 25 line 32 - col. 26 line 13, should read as:

Claim 1. A once-a-day amoxicillin antibiotic product comprising; first, second, and third amoxicillin antibiotic dosage forms, each of said amoxicillin antibiotic dosage forms comprising at least one amoxicillin antibiotic and a pharmaceutically acceptable carrier, said first amoxicillin antibiotic dosage form being[[,]] an immediate release dosage form, said second and third amoxicillin antibiotic dosage forms being delayed release[[:]] dosage forms, wherein said second amoxicillin antibiotic dosage form comprises amoxicillin coated with a methacrylic acid copolymer dispersion and said third amoxicillin antibiotic dosage form comprises amoxicillin coated with a first layer of a methacrylic acid copolymer dispersion and a second layer of hypromellose acetate succinate, and wherein each of said first, second, and third amoxicillin antibiotic dosage forms initiates release at different times, Cmax of the total amoxicillin antibiotic released from said amoxicillin antibiotic product is achieved in less [[that]] than about 12 hours from administration; wherein said product contains the total dosage of amoxicillin, for a 24-hour dosing interval.

Signed and Sealed this
Thirteenth Day of May, 2014

Michelle K. Lee
*Deputy Director of the United States Patent and Trademark Office*